United States Patent
Cohn et al.

(10) Patent No.: US 11,590,322 B2
(45) Date of Patent: Feb. 28, 2023

(54) DEVICES AND METHODS FOR ADVANCING A WIRE

(71) Applicant: TVA Medical, Inc., Austin, TX (US)

(72) Inventors: William E. Cohn, Bellaire, TX (US); Thomas D. Pate, Austin, TX (US); Philip M. Tetzlaff, Austin, TX (US)

(73) Assignee: TVA Medical, Inc., Franklin Lakes, NJ (US)

( * ) Notice: Subject to any disclaimer, the term of this patent is extended or adjusted under 35 U.S.C. 154(b) by 590 days.

(21) Appl. No.: 16/024,345

(22) Filed: Jun. 29, 2018

(65) Prior Publication Data
US 2019/0134349 A1    May 9, 2019

Related U.S. Application Data

(63) Continuation of application No. PCT/US2017/013610, filed on Jan. 15, 2017.
(Continued)

(51) Int. Cl.
*A61M 25/01* (2006.01)
*A61M 25/09* (2006.01)
*A61M 25/00* (2006.01)

(52) U.S. Cl.
CPC .... *A61M 25/0194* (2013.01); *A61M 25/0021* (2013.01); *A61M 25/09041* (2013.01);
(Continued)

(58) Field of Classification Search
CPC .......... A61M 25/0194; A61M 25/0021; A61M 25/09041; A61M 25/0127;
(Continued)

(56) References Cited

U.S. PATENT DOCUMENTS

| | | |
|---|---|---|
| 3,649,850 A | 3/1972 | Davis |
| 3,827,436 A | 8/1974 | Stumpf et al. |

(Continued)

FOREIGN PATENT DOCUMENTS

| | | |
|---|---|---|
| CA | 2883209 A1 | 4/2014 |
| CN | 1730123 A | 2/2006 |

(Continued)

OTHER PUBLICATIONS

Extended European Search Report pertaining to EP Patent Application No. 17853586.0, dated Apr. 29, 2020.
(Continued)

*Primary Examiner* — Leslie R Deak
(74) *Attorney, Agent, or Firm* — Dinsmore & Shohl LLP

(57) ABSTRACT

Systems and methods for positioning a wire for advancement through a vessel wall, and advancing it through one or more vessel walls, generally include a delivery catheter and an alignment catheter or a receiving catheter, and a guidewire. In some variations, the systems and methods may be used to bypass an occlusion or other barrier that may prevent advancement of a wire or tools through an endoluminal space. In these variations, the systems and methods include a delivery catheter, a bypass catheter, a receiving catheter, and a guidewire. The delivery and receiving catheters each generally include a side aperture, a deflection surface, and an alignment element, and the bypass catheter generally includes two side apertures, two deflectors, and two alignment elements. In some variations, the systems and methods may assist in treatment of a patient suffering from critical limb ischemia.

15 Claims, 17 Drawing Sheets

Related U.S. Application Data

(60) Provisional application No. 62/279,650, filed on Jan. 15, 2016.

(52) U.S. Cl.
CPC ... *A61M 25/0127* (2013.01); *A61M 2025/018* (2013.01); *A61M 2025/0197* (2013.01)

(58) Field of Classification Search
CPC ...... A61M 2025/0197; A61M 25/0032; A61M 25/0068
See application file for complete search history.

(56) References Cited

U.S. PATENT DOCUMENTS

| | | | |
|---|---|---|---|
| 4,416,664 A | 11/1983 | Womack | |
| 4,802,475 A | 2/1989 | Weshahy | |
| 5,180,365 A * | 1/1993 | Ensminger | A61M 39/0606 604/288.03 |
| 5,313,943 A | 5/1994 | Houser et al. | |
| 5,383,460 A | 1/1995 | Jang et al. | |
| 5,697,909 A | 12/1997 | Eggers et al. | |
| 5,782,239 A | 7/1998 | Webster, Jr. | |
| 5,800,487 A | 9/1998 | Mikus et al. | |
| 5,830,222 A | 11/1998 | Makower | |
| 5,830,224 A * | 11/1998 | Cohn | A61B 17/11 606/167 |
| 5,836,947 A | 11/1998 | Fleischman et al. | |
| 5,895,404 A | 4/1999 | Ruiz | |
| 5,971,979 A | 10/1999 | Joye et al. | |
| 6,004,330 A | 12/1999 | Middleman et al. | |
| 6,032,677 A | 3/2000 | Blechman et al. | |
| 6,039,730 A | 3/2000 | Rabin et al. | |
| 6,068,638 A | 5/2000 | Makower | |
| 6,071,274 A | 6/2000 | Thompson et al. | |
| 6,099,542 A | 8/2000 | Cohn et al. | |
| 6,159,225 A | 12/2000 | Makower | |
| 6,190,353 B1 | 2/2001 | Makower et al. | |
| 6,197,025 B1 | 3/2001 | Grossi et al. | |
| 6,217,575 B1 | 4/2001 | DeVore et al. | |
| 6,231,587 B1 | 5/2001 | Makower | |
| 6,256,525 B1 | 7/2001 | Yang et al. | |
| 6,283,988 B1 | 9/2001 | Laufer et al. | |
| 6,287,306 B1 | 9/2001 | Kroll et al. | |
| 6,302,875 B1 | 10/2001 | Makower et al. | |
| 6,327,505 B1 | 12/2001 | Medhkour et al. | |
| 6,347,247 B1 | 2/2002 | Dev et al. | |
| 6,355,029 B1 | 3/2002 | Joye et al. | |
| 6,357,447 B1 | 3/2002 | Swanson et al. | |
| 6,379,353 B1 | 4/2002 | Nichols | |
| 6,383,180 B1 | 5/2002 | Lalonde et al. | |
| 6,394,956 B1 | 5/2002 | Chandrasekaran et al. | |
| 6,400,976 B1 | 6/2002 | Champeau | |
| 6,428,534 B1 | 8/2002 | Joye et al. | |
| 6,461,356 B1 | 10/2002 | Patterson | |
| 6,464,665 B1 | 10/2002 | Heuser | |
| 6,464,723 B1 | 10/2002 | Callol | |
| 6,468,268 B1 | 10/2002 | Abboud et al. | |
| 6,475,214 B1 | 11/2002 | Moaddeb | |
| 6,475,226 B1 | 11/2002 | Belef et al. | |
| 6,527,724 B1 | 3/2003 | Fenici | |
| 6,527,769 B2 | 3/2003 | Langberg et al. | |
| 6,542,766 B2 | 4/2003 | Hall et al. | |
| 6,544,230 B1 | 4/2003 | Flaherty et al. | |
| 6,569,158 B1 | 5/2003 | Abboud et al. | |
| 6,569,162 B2 | 5/2003 | He | |
| 6,579,311 B1 | 6/2003 | Makower | |
| 6,585,650 B1 | 7/2003 | Solem | |
| 6,592,577 B2 | 7/2003 | Abboud et al. | |
| 6,629,987 B1 | 10/2003 | Gambale et al. | |
| 6,635,053 B1 | 10/2003 | Lalonde et al. | |
| 6,655,386 B1 | 12/2003 | Makower et al. | |
| 6,656,173 B1 | 12/2003 | Palermo | |
| 6,663,625 B1 | 12/2003 | Ormsby et al. | |
| 6,669,709 B1 | 12/2003 | Cohn et al. | |
| 6,673,085 B1 | 1/2004 | Berg | |
| 6,676,657 B2 | 1/2004 | Wood | |
| 6,682,525 B2 | 1/2004 | Lalonde et al. | |
| 6,695,878 B2 | 2/2004 | McGuckin et al. | |
| 6,709,444 B1 | 3/2004 | Makower | |
| 6,719,756 B1 | 4/2004 | Muntermann | |
| 6,726,697 B2 | 4/2004 | Nicholas et al. | |
| 6,733,494 B2 | 5/2004 | Abboud et al. | |
| 6,736,808 B1 | 5/2004 | Motamedi et al. | |
| 6,761,708 B1 | 7/2004 | Chiu et al. | |
| 6,761,714 B2 | 7/2004 | Abboud et al. | |
| 6,780,181 B2 | 8/2004 | Kroll et al. | |
| 6,849,073 B2 | 2/2005 | Hoey et al. | |
| 6,855,143 B2 | 2/2005 | Davison et al. | |
| 6,887,234 B2 | 5/2005 | Abboud et al. | |
| 6,911,026 B1 | 6/2005 | Hall et al. | |
| 6,932,814 B2 | 8/2005 | Wood | |
| 6,936,024 B1 | 8/2005 | Houser | |
| 6,960,209 B2 | 11/2005 | Clague et al. | |
| 6,971,983 B1 | 12/2005 | Cancio | |
| 6,981,972 B1 | 1/2006 | Farley et al. | |
| 7,059,330 B1 | 6/2006 | Makower et al. | |
| 7,060,063 B2 | 6/2006 | Marion et al. | |
| 7,094,235 B2 | 8/2006 | Francischelli | |
| 7,155,293 B2 | 12/2006 | Westlund et al. | |
| 7,179,270 B2 | 2/2007 | Makower | |
| 7,189,231 B2 | 3/2007 | Clague et al. | |
| 7,214,234 B2 | 5/2007 | Rapacki et al. | |
| 7,231,260 B2 | 6/2007 | Wallace et al. | |
| 7,250,051 B2 | 7/2007 | Francischelli | |
| 7,288,075 B2 | 10/2007 | Parihar et al. | |
| 7,303,554 B2 | 12/2007 | Lalonde et al. | |
| 7,306,598 B2 | 12/2007 | Truckai et al. | |
| 7,335,198 B2 | 2/2008 | Eggers et al. | |
| 7,341,063 B2 | 3/2008 | Garbibaldi et al. | |
| 7,367,341 B2 | 5/2008 | Anderson et al. | |
| 7,374,567 B2 | 5/2008 | Heuser | |
| 7,387,636 B2 | 6/2008 | Cohn et al. | |
| 7,407,506 B2 | 8/2008 | Makower | |
| 7,522,950 B2 | 4/2009 | Fuimaono et al. | |
| 7,628,768 B2 | 12/2009 | Faul et al. | |
| 7,702,387 B2 | 4/2010 | Stevenson et al. | |
| 7,727,268 B2 | 6/2010 | Cunniffe et al. | |
| 7,744,596 B2 | 6/2010 | Young et al. | |
| 7,811,281 B1 | 10/2010 | Rentrop | |
| 7,828,814 B2 | 11/2010 | Brenneman et al. | |
| 7,846,172 B2 | 12/2010 | Makower | |
| 7,849,860 B2 | 12/2010 | Makower et al. | |
| 7,857,809 B2 | 12/2010 | Drysen | |
| 7,881,797 B2 | 2/2011 | Griffin et al. | |
| 7,955,326 B2 | 6/2011 | Paul et al. | |
| 7,967,769 B2 | 6/2011 | Faul et al. | |
| 7,967,770 B2 | 6/2011 | Li et al. | |
| 8,010,208 B2 | 8/2011 | Nimer et al. | |
| 8,048,016 B2 | 11/2011 | Faul et al. | |
| 8,052,680 B2 | 11/2011 | Hassett et al. | |
| 8,062,321 B2 | 11/2011 | Heuser et al. | |
| RE43,007 E | 12/2011 | Lalonde et al. | |
| 8,075,555 B2 | 12/2011 | Truckai et al. | |
| 8,088,171 B2 | 1/2012 | Brenneman | |
| 8,100,899 B2 | 1/2012 | Doty et al. | |
| 8,118,809 B2 | 2/2012 | Paul et al. | |
| 8,135,467 B2 | 3/2012 | Markowitz et al. | |
| 8,142,454 B2 | 3/2012 | Harrison et al. | |
| 8,192,425 B2 | 6/2012 | Mirza et al. | |
| 8,200,466 B2 | 6/2012 | Spilker et al. | |
| 8,226,592 B2 | 7/2012 | Brenneman et al. | |
| 8,231,618 B2 | 7/2012 | Viswanathan et al. | |
| 8,236,014 B2 | 8/2012 | Brenneman et al. | |
| 8,262,649 B2 | 9/2012 | Francischelli | |
| 8,273,095 B2 | 9/2012 | Brenneman et al. | |
| 8,328,797 B2 | 12/2012 | Wilson et al. | |
| 8,333,758 B2 | 12/2012 | Joye et al. | |
| 8,361,061 B2 | 1/2013 | Esch et al. | |
| 8,366,707 B2 | 2/2013 | Kassab et al. | |
| 8,382,697 B2 | 2/2013 | Brenneman et al. | |
| 8,409,196 B2 | 4/2013 | Durgin et al. | |
| 8,413,664 B2 | 4/2013 | Appling | |

(56) References Cited

U.S. PATENT DOCUMENTS

| | | |
|---|---|---|
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,510,901 B2 | 12/2016 | Steinke et al. |
| 9,623,217 B2 | 4/2017 | Pillai |
| 9,675,378 B2 * | 6/2017 | Hart ............... A61B 17/3421 |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Peña |
| 10,596,356 B2 | 3/2020 | Lenihan et al. |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0193140 A1 * | 9/2004 | Griffin ............ A61M 25/0068 |
| | | 604/524 |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0221519 A1 | 9/2008 | Schwach et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0157014 A1 | 6/2009 | Osborne et al. |
| 2009/0187098 A1 | 7/2009 | Makower et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2010/0318180 A1 | 12/2010 | Porter |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1 * | 11/2012 | Miller ............. A61B 18/1492 |
| | | 604/8 |
| 2013/0041306 A1 | 2/2013 | Faul et al. |

(56) References Cited

U.S. PATENT DOCUMENTS

| | | |
|---|---|---|
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2013/0296704 A1 | 11/2013 | Magnin et al. |
| 2014/0012251 A1 | 1/2014 | Himmelstein et al. |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios et al. |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0126965 A1 | 5/2015 | Liungman |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196309 A1 | 7/2015 | Matsubara et al. |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0051323 A1 | 2/2016 | Stigall et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0100840 A1 | 4/2016 | Brenneman et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1 | 7/2016 | Dickinson et al. |
| 2017/0071627 A1 | 3/2017 | Kellerman et al. |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2017/0232272 A1 | 8/2017 | Perkins et al. |
| 2017/0252006 A1 | 9/2017 | Tsuruno |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0038103 A1 | 2/2020 | Pappone et al. |
| 2020/0061338 A1 | 2/2020 | Pate |
| 2020/0178970 A1 | 6/2020 | Berman et al. |

FOREIGN PATENT DOCUMENTS

| | | |
|---|---|---|
| CN | 101730557 A | 6/2010 |
| EP | 0923912 A2 | 6/1999 |
| RU | 2168951 C1 | 6/2001 |
| WO | 9729682 A1 | 8/1997 |
| WO | 9956640 A1 | 11/1999 |
| WO | 2006105008 A1 | 10/2006 |
| WO | 2008010039 A2 | 1/2008 |
| WO | 2009005644 A2 | 1/2009 |
| WO | 2011100625 A2 | 8/2011 |
| WO | 2013112584 A1 | 8/2013 |
| WO | 2014028306 A1 | 2/2014 |
| WO | 2014052919 A1 | 4/2014 |
| WO | 2015061614 A1 | 4/2015 |
| WO | 2015085119 A1 | 6/2015 |
| WO | 2015108984 A1 | 7/2015 |
| WO | 2016033380 A1 | 3/2016 |
| WO | 2016081321 A2 | 5/2016 |
| WO | 2017124059 A1 | 7/2017 |
| WO | 2017124060 A1 | 7/2017 |
| WO | 2018057095 A1 | 3/2018 |

OTHER PUBLICATIONS

Maybury et al., "The Effect of Roll Angle on the Performance of Halbach Arrays," University of California—San Diego, Center for Magnetic Recording Research (2008), 19 pgs.

Choi, et al., Design of a Halbach Magnet Array Based on Optimization Techniques; IEEE Transactions on Magnetics, vol. 44, No. 10, Oct. 2008, pp. 2361-2366. (Year: 2008).

"Banasik et al. (2011). ""A rare variant route of the ulnar artery does not contraindicate the creation of a fistula in the wrist of a diabetic patient with end-stage renal disease,"" Postepy Hig Med Dosw. 65:654-657."

Bharat et al. (2012) "A novel technique of vascular anastomosis to prevent juxta-anastomotic stenosis following arteriovenous fistula creation," J. Vascular Surgery 55(1):274-280.

Bode et al. (2011 ). "Clinical study protocol for the arch project Computational modeling for improvement of outcome after vascular access creation," J. Vase. Access 12(4):369-376.

Hakim et al., "Ulnar artery-based free forearm flap: Review of Specific anatomic features in 322 cases and related literature," Heand & Neck, Dec. 2013 (published online:2014), Wiley Online Library.

Davidson, I. et al. (2008). "Duplex Ultrasound Evaluation for Dialysis Access Selection and Maintenance: A Practical Guide," The Journal of Vascular Access 9(1 ): 1-9.

Gracz, et al. (1977). "Proximal forearm fistula for maintenance hemodialysis," Kidney International 11 :71-75.

Jennings, WC. et al. (2011). "Primary arteriovenous fistula inflow proximalization for patients at high risk for dialysis access-associated ischemic steal syndrome," J. Vase. Surgery 54(2):554-558.

Kinnaert, et al. (1971). "Ulnar Arteriovenous Fistula for Maintenance Haemodial ysis," British J. Surgery 58(9):641-643.

Morale et al. (2011). "Venae comitantes as a potential vascular resource to create native arteriovenous fistulae," J. Vase. Access 12(3):211-214.

Shenoy, S. (2009). "Surgical anatomy of upper arm: what is needed for AVF planning," The Journal of Vascular Access 10:223-232.

Vachharajani, T. (2010). "Atlas of Dialysis Vascular Access," Wake Forest University School of Medicine, 77 total pages.

Whittaker et al. (2011). "Prevention better than cure. Avoiding steal syndrome with proximal radial or ulnar arteriovenous fistulae" J. Vase. Access 12(4):318-320.

International Search Report and Written Opinion pertaining to PCT/US2019/034896, dated May 12, 2020.

Extended European Search Report for EP Application No. 17739123.2.

Office Action pertaining to corresponding Japanese Patent Application No. 2018-536423, dated Feb. 12, 2021.

\* cited by examiner

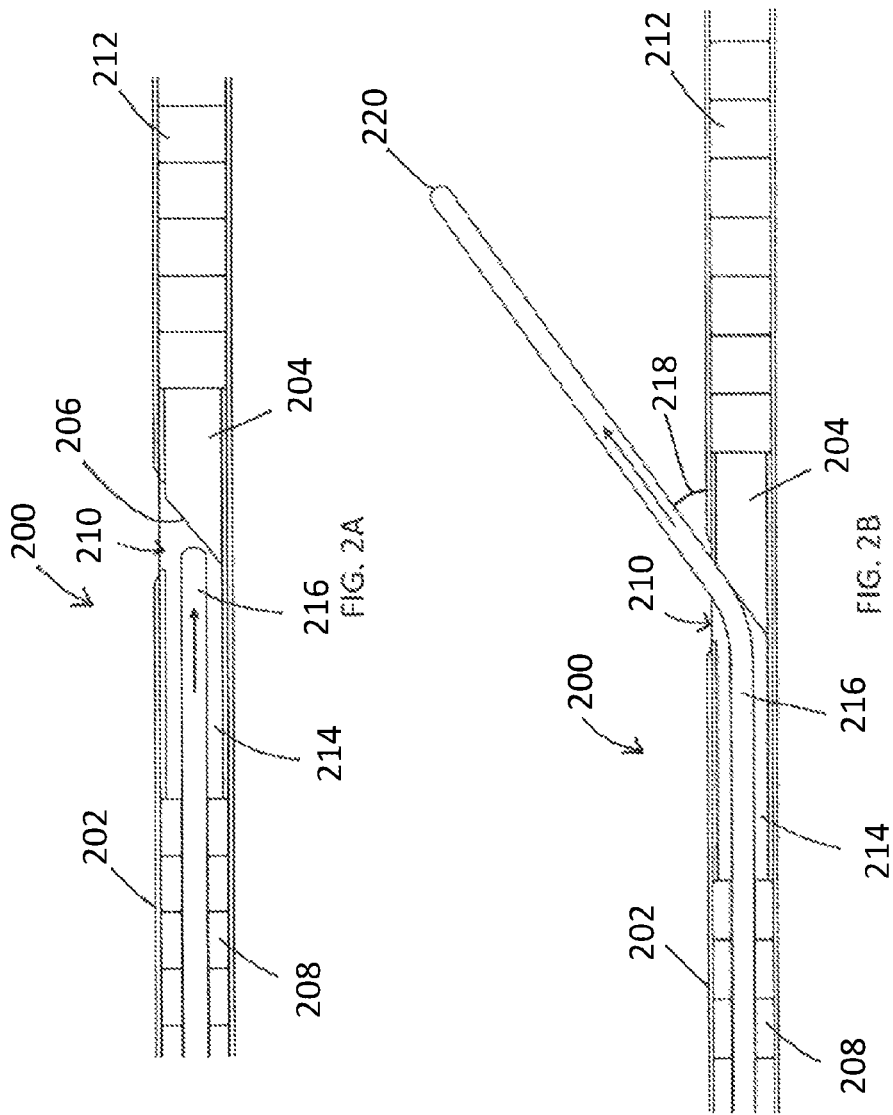

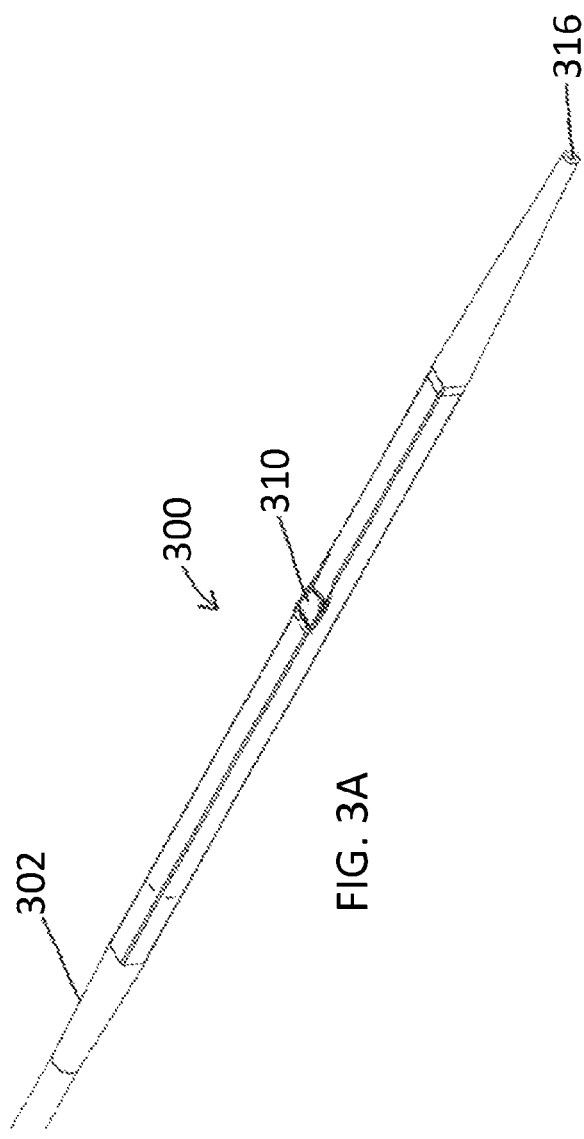
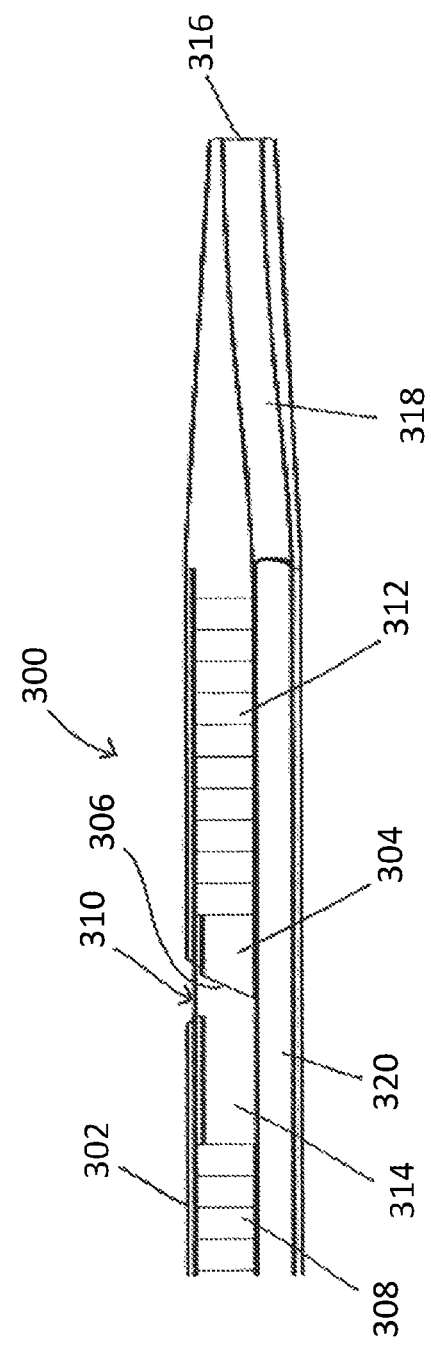
FIG. 3A
FIG. 3B

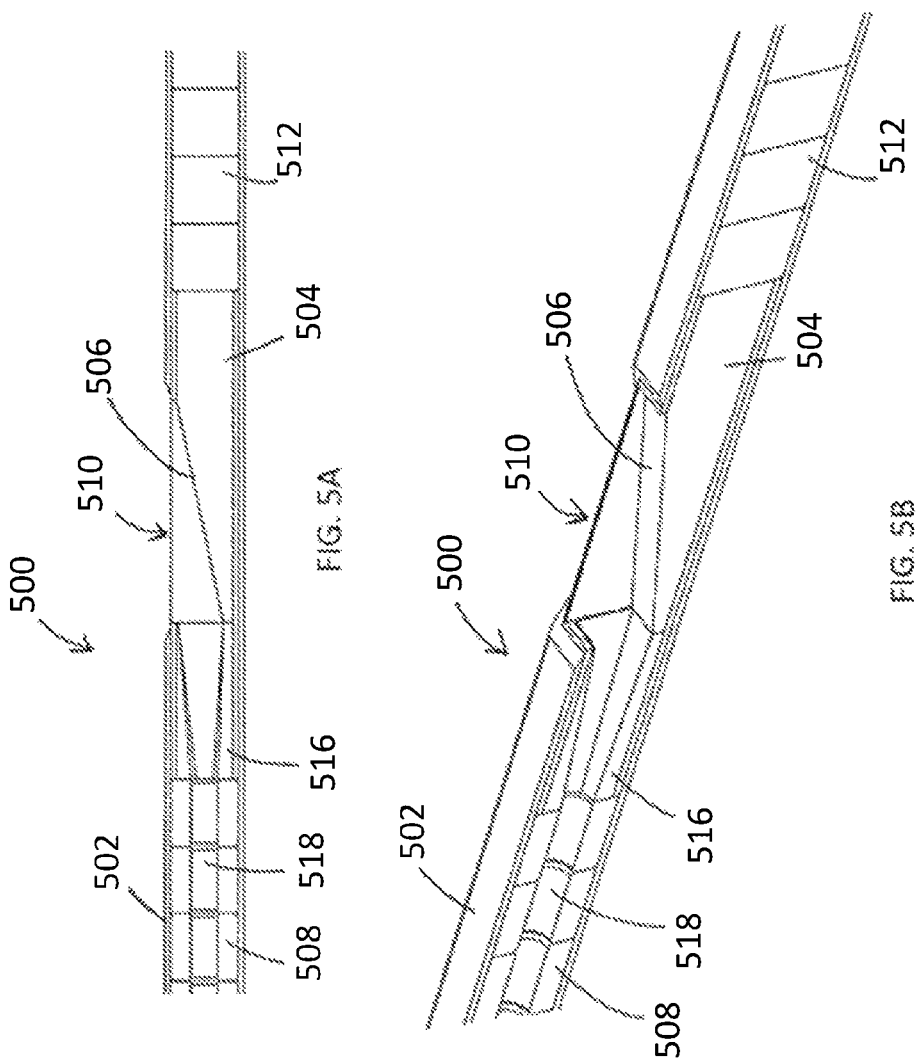

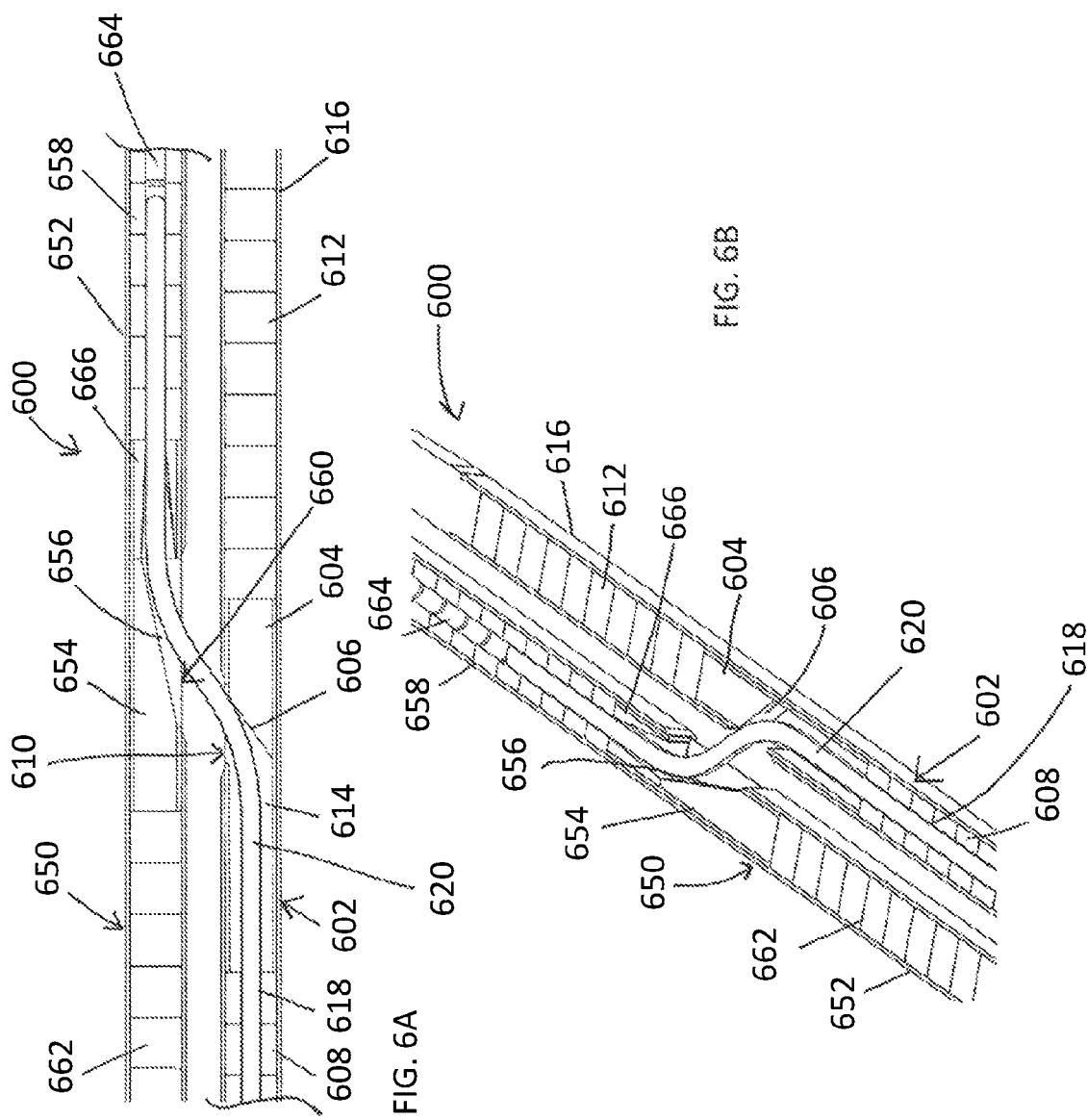

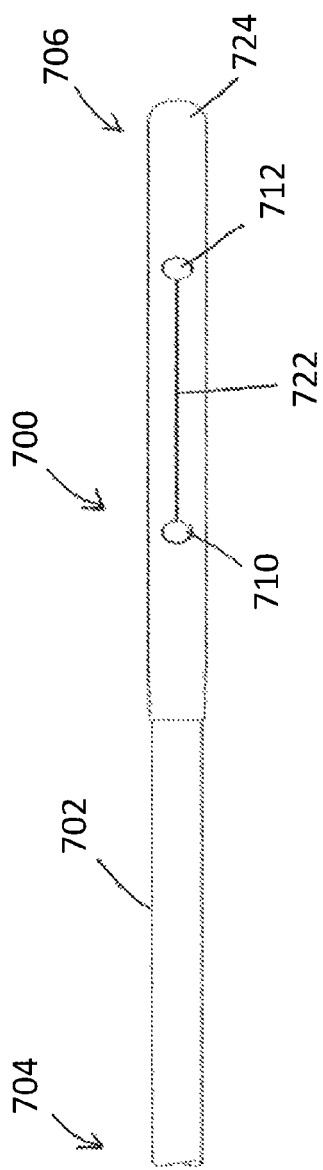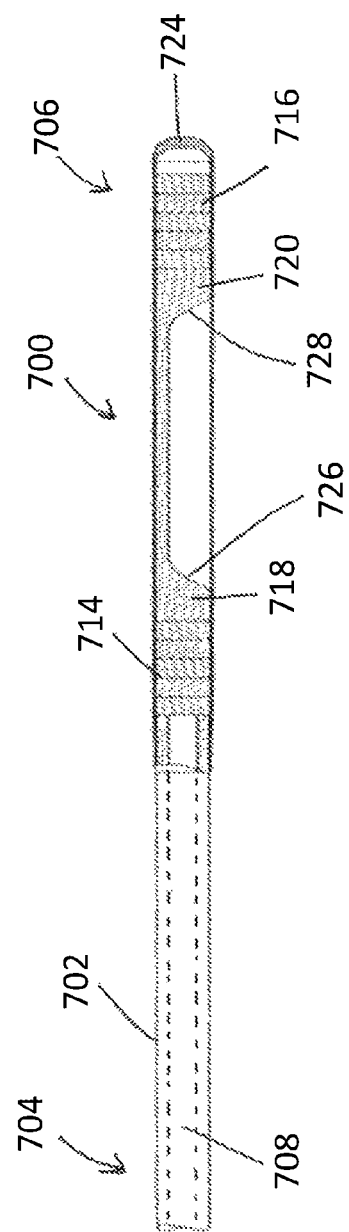

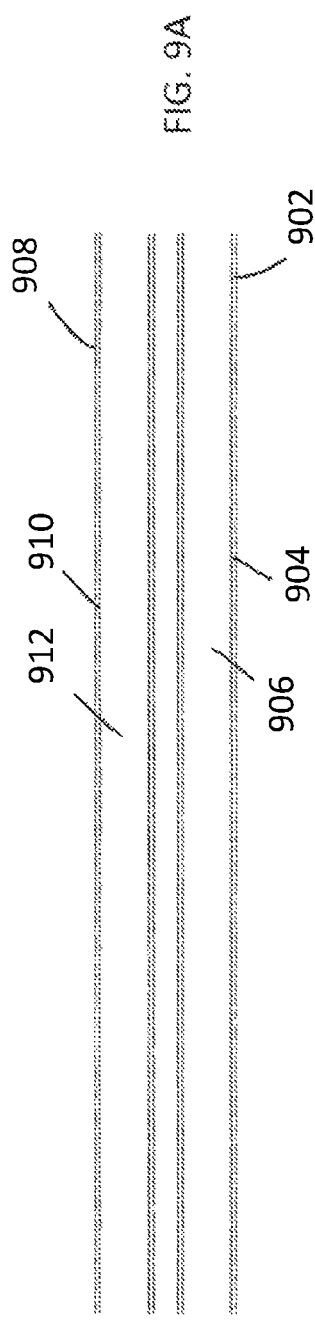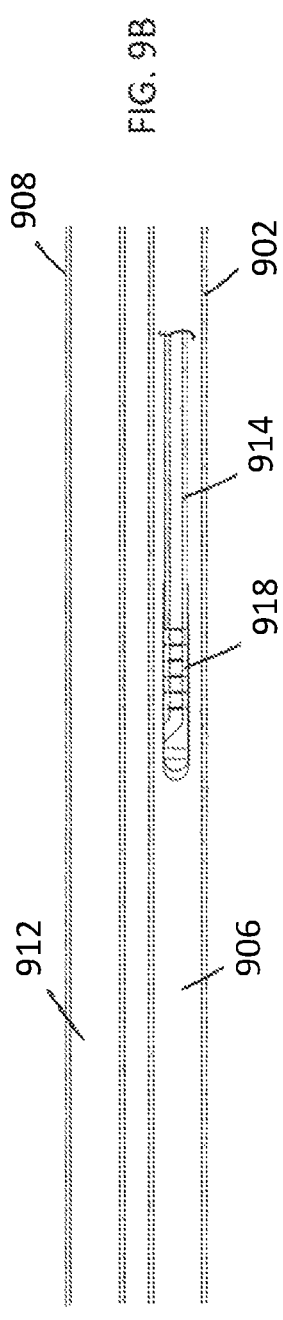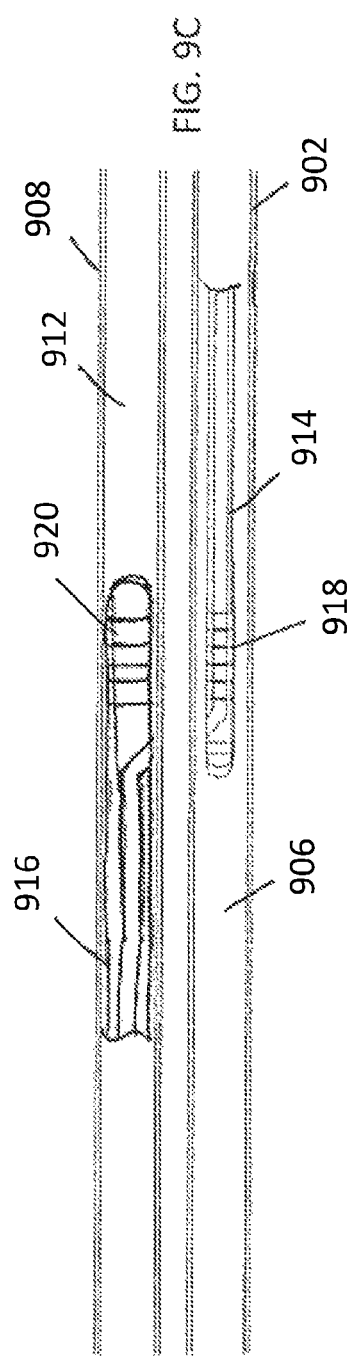

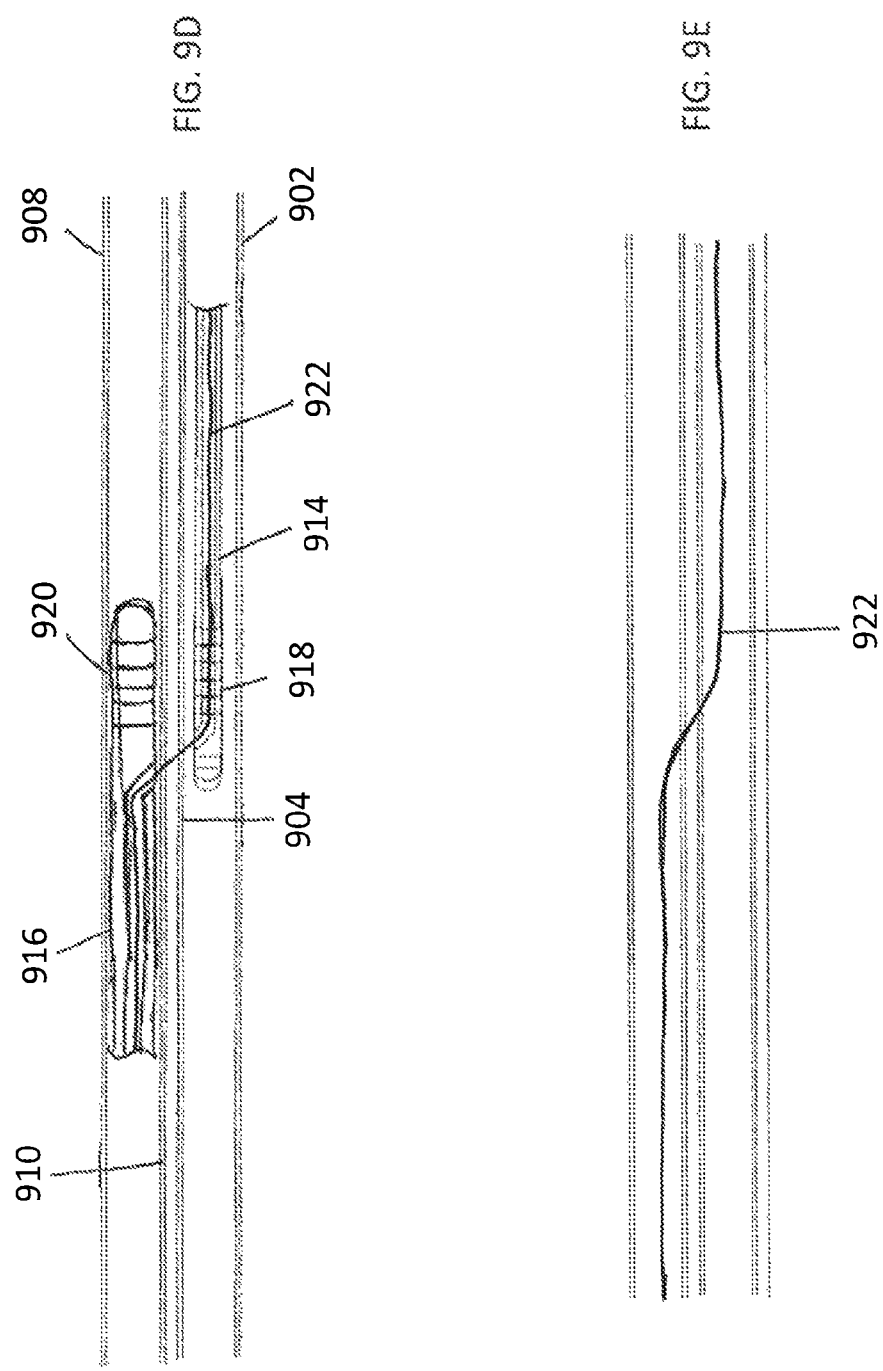

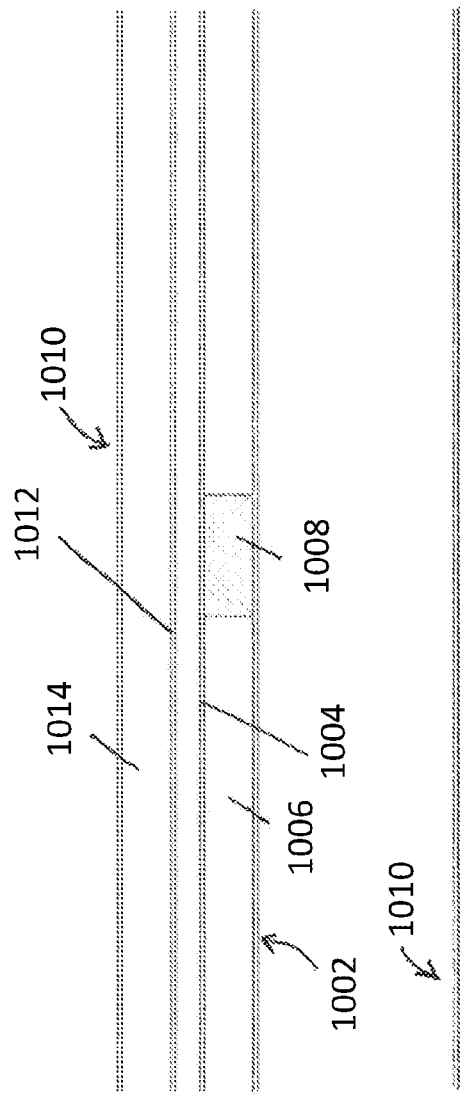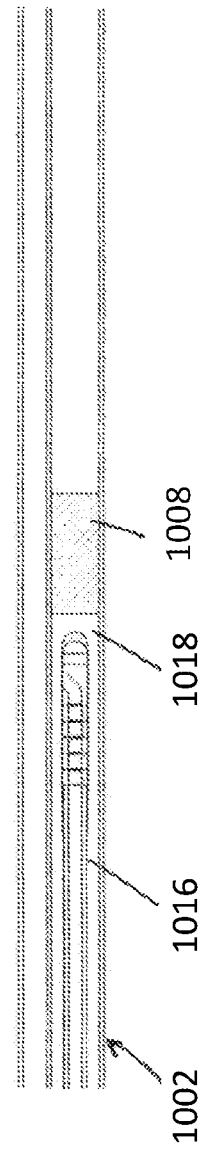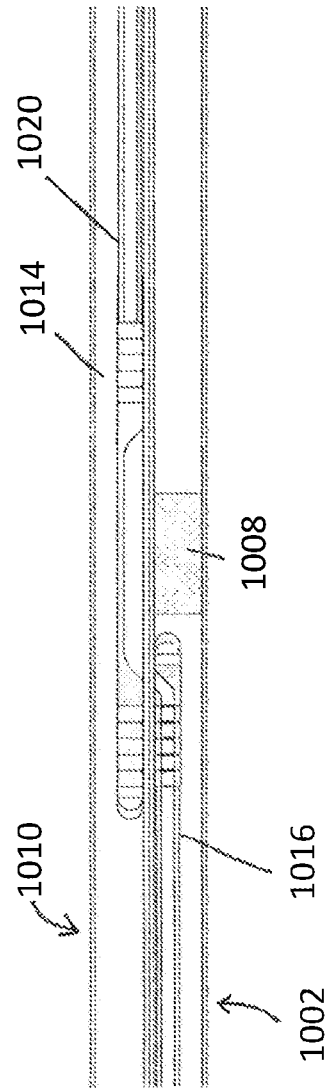

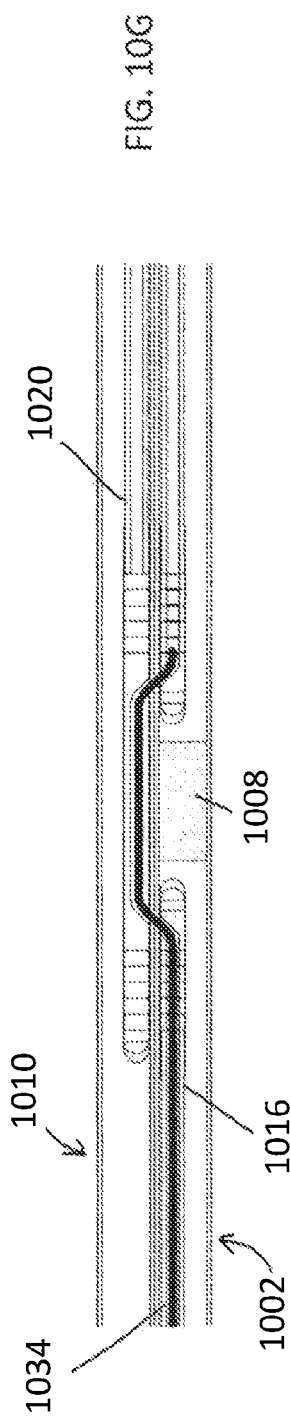
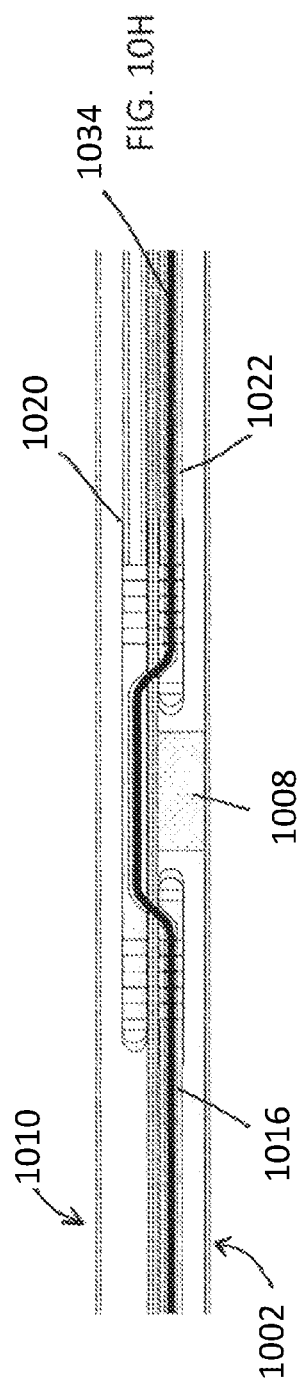
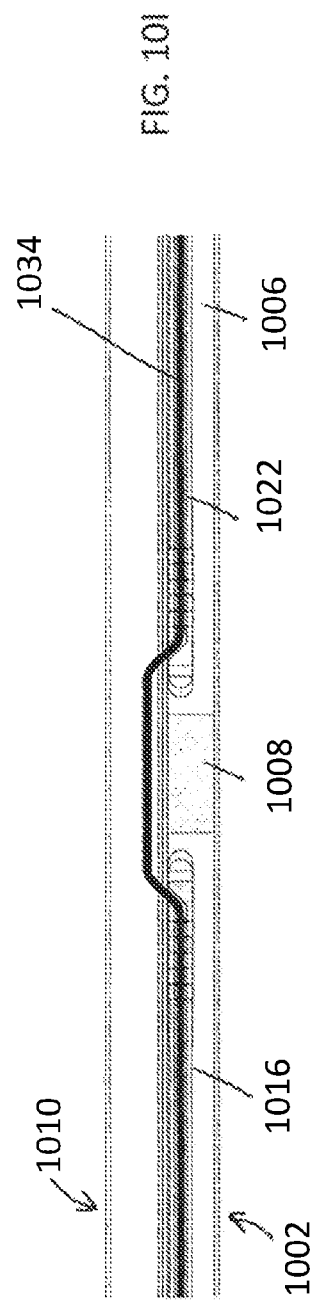

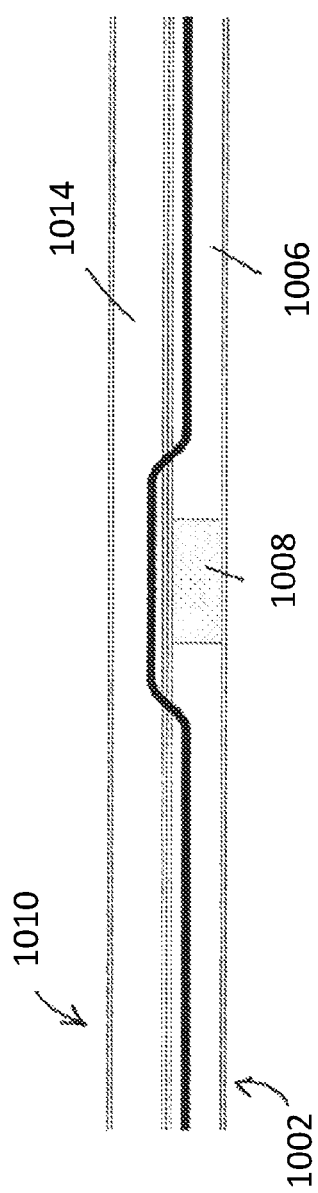

DEVICES AND METHODS FOR ADVANCING A WIRE

CROSS-REFERENCE TO RELATED APPLICATIONS

This application is a continuation of International Application No. PCT/US2017/013610, filed on Jan. 15, 2017, which claims priority to U.S. Provisional Application Serial No. 62/279,650, filed on Jan. 15, 2016, and titled "DEVICES AND METHODS FOR ADVANCING A WIRE," the contents of each of which are hereby incorporated by reference in their entirety.

FIELD

The current invention relates to systems and methods for advancing a wire. The systems and methods may be used to advance a wire through one or more vessel walls, for example to bypass an occlusion in a vessel.

BACKGROUND

During some percutaneous procedures, it may be necessary or desirable to advance tools from a first vessel (e.g., a vein or artery) to a second, nearby vessel (e.g., a second vein or artery). This may be especially desirable in procedures to form a fistula between the two vessels. A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Accordingly, it may therefore be useful to find improved ways to access or and form a path between two vessels that may be used during fistula creation.

Additionally, it may be necessary or desirable to form a path between two blood vessels to avoid or bypass an occlusion or barrier within one of the vessels to effectuate treatment of a variety of diseases. People may suffer from occluded vessels for a number of reasons, including peripheral vascular disease (PVD), which may progress into critical limb ischemia (CLI) if left untreated. CLI is characterized by chronic pain, as well as tissue loss that may ultimately result in amputation. Amputations are not only costly, they also lead to a significant loss in quality of life for the amputee, and in some unfortunate cases, result in a patient's death. Accordingly, it may therefore be useful to find improved ways to access and create alternate paths for blood flow around an occlusion.

To form a path between two vessels or between a vessel and a cavity, it may be necessary or desirable to deliver a guidewire or a needle from a first vessel lumen or cavity to another vessel lumen or cavity with high accuracy. This may prevent unnecessary or inaccurate punctures. For example, during passage of a guidewire from the abdominal inferior vena cava into the aorta, the guidewire should be accurately delivered from the vena cava to the aorta to prevent potentially damaging inaccurate or unnecessary punctures in the vena cava and/or the aorta. Additionally, high accuracy systems and methods may also assist with delivery of a guidewire or needle to small vessels, as accessing and puncturing vessels may become more difficult as vessel diameter decreases. In larger vessels, it may be difficult to create a path between vessels if the tools are not located close enough to the vessel walls or if the vessel walls themselves have too much space between them. Thus, at times, it may be beneficial to move the vessels closer together before a path between the vessels is created, or for the tools used to be located close to the vessel walls, as this may result in a decreased travel distance for the guidewire or needle to create a desired path and/or may result in fewer alignment errors. Accordingly, it may be useful to find accurate systems and methods for delivering a wire to a target location and for creating a pathway between vessels. Additionally, systems and methods that decrease the distance between vessels or between tools and vessel walls during path formation may be useful.

In some instances, increased system complexity or utilization of multiple modes of visualization may be undesirable in the clinical setting. Accordingly, it may be useful to develop systems and methods that are simple and do not require significant time or effort for alignment for successful delivery into a desired location.

BRIEF SUMMARY

Described here are systems and methods for advancing a wire through luminal walls from a first endoluminal space to a second endoluminal space and for many uses, including bypassing an occlusion or barrier in a vessel. Generally, systems described here may comprise a plurality of catheters. In some variations, the systems and methods described here may comprise a first catheter and a second catheter. In other variations, the system and methods described here may comprise a first catheter, a second catheter, and a third catheter.

In some variations, the systems described here may comprise a first catheter, a second catheter, and a guidewire. The first catheter may comprise a catheter body having a first lumen therethrough and a first side aperture, a first deflection surface, and a first alignment element. The second catheter may comprise a catheter body having a second lumen therethrough and a second side aperture, a second deflection surface, and a second alignment element. The third catheter may comprise a catheter body having a lumen therethrough, a fourth side aperture, a fourth deflector positioned within the lumen, and a fourth alignment element. In some variations, the first and second alignment elements may be configured to align the first and second side apertures to create a guidewire pathway through the first and second catheters.

In some variations, the first catheter is a delivery catheter and the second catheter is a receiving catheter. The first and second alignment elements may each comprise a magnet or magnetic array. In some variations, the first catheter may further comprise a third alignment element and the second catheter may comprise a fourth alignment element. In some of these variations, the third and fourth alignment elements may each comprise a magnet or a magnetic array. The first alignment element may be positioned proximal to the first side aperture and the third alignment element may be positioned distal to the first side aperture. The first deflection surface may be positioned between the first and third alignment elements. The second alignment element may be positioned distal to the second side aperture and the fourth alignment element may be positioned proximal to the second side aperture. The second deflection surface may be positioned between the second and fourth alignment elements. In other of these variations, the first alignment element may be configured to mate with the second alignment element and the third alignment element may be configured to mate with the fourth alignment element. The first and second catheters are configured to be aligned lengthwise. In another of these variations, the first alignment element may comprise a lumen configured to pass the guidewire therethrough. The fourth alignment element may comprise a lumen configured to pass the guidewire therethrough.

The system may include one or more additional features. In some variations, the first catheter may comprise a first deflector positioned within the first lumen and comprise the first deflection surface and the second catheter may comprise a second deflector positioned within the second lumen and comprising the second deflection surface. In some variations, the first and second catheters may be arranged so that slopes of the first and second deflection surfaces have the same sign. In some variations, one or both of the first and second deflection surface may be curved. In some variations, the second catheter may further comprise a guide funnel configured to direct a distal tip of the guidewire into the second lumen. The first and second catheters may each comprise an atraumatic tip.

Also described herein are other systems for bypassing an occlusion in a vessel. In general, these systems may comprise a first catheter, a second catheter, a third catheter, and a guidewire. The first catheter may comprise a catheter body having a first lumen therethrough and a first side aperture, and a first alignment element. The second catheter may comprise a catheter body having a second lumen therethrough and second and third side apertures, and second and third alignment elements. The third catheter may comprise a catheter body having a third lumen therethrough and a fourth side aperture, and a fourth alignment element. In some variations, the first and second alignment elements may be configured to align the first and second side apertures. The third and fourth alignment elements may be configured to align the third and fourth side apertures to create a guidewire pathway through the first, second, and third catheters.

In some variations, the first catheter may be a delivery catheter, the second catheter may be a bypass catheter, and the third catheter may be a receiving catheter. The first, second, third, and fourth alignment elements may each comprise a magnet or a magnetic array. The second catheter may comprise a slit, a weakened body portion, or perforations between the second and third side apertures.

In some variations, the first catheter may further comprise a first deflector positioned within the first lumen, the second catheter may further comprise second and third deflectors positioned within the second lumen, and the third catheter may further comprise a fourth deflector positioned within the fourth lumen. In some of these variations, the first, second, third, and fourth deflectors may each comprise a deflection surface. In another of these variations, the first, second, and third catheters may be arranged so that slopes of three of the deflection surfaces have the same sign and a slope of the fourth deflection surface has the opposite sign.

In other of these variations, the first, second, and third catheters may be arranged so that the first deflector comprises a first deflection surface with a positive slope, the second deflector comprises a second deflection surface with a negative slope, the third deflector comprises a third deflection surface with a positive slope, and the fourth deflector comprises a fourth deflection surface with a positive slope. Positive may be defined as increasing from a proximal end to a distal end and negative may be defined as decreasing from a proximal end to a distal end. In another of these variations, one or more of the first, second, third, and fourth deflection surfaces may be curved.

In other of these variations, each of the second and third deflectors may comprise a deflection surface. One of the deflection surfaces may have a positive slope and the other of the deflection surfaces may have a negative slope. Positive may be defined as increasing from a proximal end to a distal end and negative may be defined as decreasing from a proximal end to a distal end. In some of these variations, the second and third deflectors may be integrally formed.

In other of these variations, the first deflector may be positioned distal to the first alignment element. In some of these variations, the second deflector may be positioned distal to the second alignment element and the third deflector may be positioned between the second and third alignment elements. In another of these variations, the fourth deflector may be positioned distal to the fourth alignment element.

In other of these variations, at least one of the second and third deflectors may comprise a lumen configured to pass a second guidewire therethrough. In some other of these variations, at least one of the second and third deflectors may be sized and positioned to allow passage of a second guidewire within the lumen of the second catheter around the at least one of the second and third deflectors.

In some variations, at least one of the first and fourth alignment elements may comprise a lumen configured to pass the guidewire therethrough. In some variations, the first, second, and third catheters may each comprise an atraumatic tip. In some variations, at least one of the second and third alignment elements may be sized and positioned to allow passage of a second guidewire within the lumen of the second catheter around the at least one of the second and third deflectors.

Generally, methods for bypassing an occlusion in a vessel may comprise advancing a first catheter through a lumen in a first vessel to a first side of the occlusion. The first catheter may comprise a first alignment element and a catheter body having a lumen therethrough and a first side aperture. A second catheter may be advanced through a lumen in a second vessel. The second catheter may comprise second and third alignment elements and a catheter body having a lumen therethrough and second and third side apertures. A third catheter may be advanced through the lumen in the first vessel to a second side of the occlusion. The third catheter may comprise a fourth alignment element and a catheter body having a lumen therethrough and a fourth side aperture. The first and second alignment elements and the third and fourth alignment elements may be aligned to create a guidewire path that bypasses the occlusion. The guidewire path may include the first, second, third, and fourth side apertures. A guidewire may be advanced along the guidewire path to form a guidewire bypass around the occlusion.

In some variations, advancing the guidewire along the guidewire path may comprise piercing a wall of the first vessel with the guidewire at a location proximal to the occlusion, piercing a wall of the second vessel with the guidewire such that the guidewire enters the second vessel lumen, advancing the guide wire through the second vessel lumen at the location of the occlusion in the first vessel, piercing the wall of the second vessel with the guidewire such that the guidewire exits the second vessel lumen, and piercing the wall of the first vessel at a location distal to the occlusion.

In some variations, the first vessel may be an artery and the second vessel may be a vein. The first vessel may be a vein and the second vessel may be an artery. In some variations, after advancing the guidewire along the guidewire path, the second catheter may be removed without disrupting the guidewire bypass. One or more of the first, second, third, and fourth alignment elements may comprise a magnet or magnetic array. Aligning the first and second alignment elements may align the first and second catheters axially and rotationally. In some of these variations, aligning the third and fourth alignment elements may align the second and third catheters axially and rotationally.

In some variations, aligning the first and second alignment elements and the third and fourth alignment elements may comprise moving the first and second vessels closer to one another. In other variations, aligning the first and second alignment elements and the third and fourth alignment elements may comprise compressing tissue of the first and second vessels. In some of these variations, the first, second, and third catheters may comprise flat alignment surfaces configured to aid in compressing tissue of the first and second vessels.

In some variations, advancing the first, second, and third catheters may occur under indirect visualization. In some variations, advancing the second and third catheters may comprise advancing the second and third catheters to an anti-parallel orientation relative to one another. In some variations, advancing the first and second catheters may comprise advancing the first and second catheters to a parallel orientation relative to one another. In some variations, after advancement of the first, second, and third catheters, two catheters may be in a parallel orientation relative to one another and two catheters may be in an anti-parallel orientation relative to one another. In some variations, the methods described herein may be performed on a patient suffering from critical limb ischemia.

Also described herein are other systems for advancing a guidewire through a vessel wall. In general, these systems may comprise a first catheter, a second catheter, and a guidewire. A first catheter may comprise a catheter body having a lumen therethrough and a side aperture, and a first alignment element. A second catheter may comprise a catheter body and a second alignment element. A guidewire may be slidably positioned within the first lumen. The first and second alignment elements may be configured to coapt to compress the vessel wall between the first and second catheters and position the side aperture for advancement of the guidewire through the vessel wall.

In some variations, the first catheter may be a delivery catheter and the second catheter may be an alignment catheter. In some variations, the first and second alignment elements may each comprise a magnet or a magnetic array. In some of these variations, the first alignment element may be positioned distal to the side aperture.

In some variations, the first catheter may further comprise a deflection surface distal to the side aperture. In some of these variations, the first alignment element may be positioned distal to the deflection surface. In other of these variations, the first catheter may further comprise a deflector positioned within the lumen and comprising the deflection surface. In yet other of these variations, the deflection surface may be curved.

In some variations, the catheters may be configured to be aligned lengthwise. The guidewire may comprise a sharpened distal tip. In some variations, the system may further comprise a flexible needle. In some of these variations, the guidewire may be slideably disposed within a lumen of the flexible needle.

In some variations, the first and second catheters may each comprise an atraumatic tip. At least a portion of each of the catheter bodies of the first and second catheters may comprise a square cross-sectional shape. In some of these variations, a distal portion of the first catheter body and a distal portion of the second catheter body may each comprise a square cross-sectional shape.

Also described herein are other systems for advancing a guidewire through a vessel wall. In general, these systems may comprise a first catheter, a second catheter, a flexible needle, and a guidewire. A first catheter may comprise a catheter body having a lumen therethrough and a side aperture, a deflector may be positioned within the lumen and comprise a deflection surface, and a first magnetic alignment element. A second catheter may comprise a catheter body and a second magnetic alignment element. A flexible needle may comprise a lumen therethrough. The flexible needle may be slideably disposed within the lumen of the first catheter. A guidewire may be slidably positioned within the lumen of the flexible needle. The first and second magnetic alignment elements may be configured to coapt to compress the vessel wall between the first and second catheters and position the side aperture for advancement of the needle and guidewire through the vessel wall.

BRIEF DESCRIPTION OF THE DRAWINGS

FIGS. 2A and 2B show illustrative cross-sectional views of a variation of a delivery catheter as a wire is advanced therethrough.

FIGS. 3A and 3B depict a perspective view and an illustrative cross-sectional view, respectively, of a variation of a catheter.

FIGS. 5A and 5B depict side cross-sectional and perspective cross-sectional views, respectively, of a variation of a receiving catheter.

FIGS. 6A and 6B show side cross-sectional and perspective cross-sectional views, respectively, of a variation of a two-catheter system.

FIG. 7A depicts a top view of a variation of a catheter suitable for use as a bypass catheter. FIG. 7B depicts a partially transparent view of the catheter depicted in FIG. 7A.

FIGS. 9A-9E depict a variation of a method for forming a path between two vessels that may be used to guide tools or devices.

FIGS. 10A-10J depict a variation of a method for bypassing an occlusion in a vessel.

DETAILED DESCRIPTION

Figure 1A:
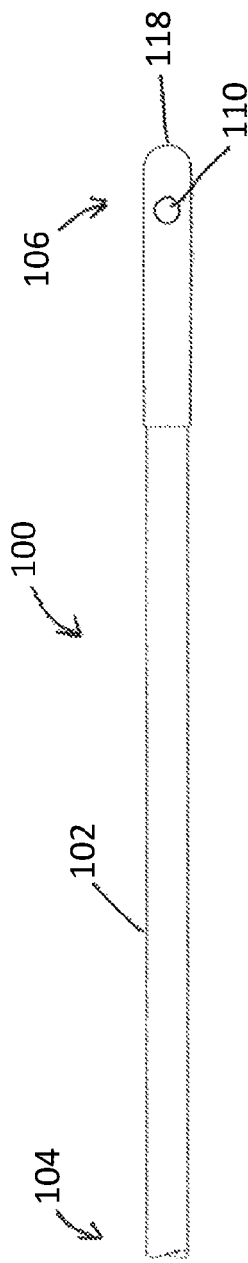
FIG. 1A depicts a top view of a variation of a catheter that may be used in the systems and methods described here.

Generally described here are systems and methods for positioning a wire for advancement through a vessel wall, and advancing it through one or more vessel walls. In some variations, the systems and methods may be used to position a wire within a first endoluminal space (e.g., blood vessel, intestine, or the like), and advance the wire from within the first endoluminal space across the luminal wall(s) into a cavity or a second endoluminal space. In some variations, the systems and methods may be used to form a fistula between two blood vessels (e.g., an arteriovenous fistula between an artery and a vein or a veno-venous fistula between two veins). For example, the systems and methods may be used to form an arteriovenous fistula to treat critical limb ischemia (CLI), chronic total occlusion (CTO), or to increase venous graft flow.

Generally, to form a path between two blood vessels, one or more catheters may be advanced in a minimally invasive fashion through the vasculature to a target location. In some instances, a system comprising two catheters may be used to form a path between a vessel and a cavity or between two vessels. For example, in some instances, the catheters may be placed on opposite sides of a vessel wall or within the lumens of adjacent vessels to form a path between the vessel and the cavity or between the two vessels. In these instances, it should be appreciated that each catheter may or may not have the same configuration of elements, and that some catheters may be different from and/or complementary to other catheters, as will be described in more detail below.

Also generally described here are systems and methods for bypassing an occlusion or other barrier that may prevent advancement of a wire or tools through an endoluminal space. For example, the systems and methods may be used to position a wire proximal to an occlusion or barrier in the lumen of the endoluminal space, advance the wire through one or more endoluminal walls into a second endoluminal space or a cavity, advance the wire through the second endoluminal space or cavity to avoid the occlusion or barrier in the first endoluminal space, and advance the wire such that it reenters the first endoluminal space on the opposite side of the occlusion or barrier. In some variations, the systems and methods may be used to advance a wire from an artery to a vein, back into the artery, or vice versa, to bypass an occlusion in the artery or vein and establish a path for tools and devices around the occlusion. For example, the systems and methods described here may be used to place a wire (e.g., a guidewire) around an occlusion so that stents or stent grafts, balloons (including cutting balloons), cutting, punching, or coring tools, or ablating devices may be advanced along the guidewire around the occlusion. The systems and methods described here may also be used for other bypass procedures, for example, femoral popliteal (fem-pop) bypass surgery.

Generally, to form a path around an occlusion or barrier, a plurality of catheters may be advanced in a minimally invasive fashion through the vasculature to a target location, e.g., at or near the occlusion or barrier. In some instances, a system comprising three catheters may be used to position a guidewire with respect to the occlusion or barrier and to establish a path around the occlusion or barrier. For example, a first catheter may be advanced within the occluded vessel to a first, proximal side of the occlusion or barrier, a second catheter may be advanced through an adjacent (or otherwise nearby) vessel or cavity, and a third catheter may be advanced within the occluded vessel to the opposite, distal side of the occlusion or barrier, and a guidewire may be advanced to create a path around the occlusion or barrier through the adjacent vessel or cavity. It should be appreciated that each of the catheters may or may not have the same or similar configuration of elements, and that some catheters may be different from and/or complementary to other catheters, as will described in more detail below.

As mentioned above, a plurality of the catheters described here may be used to create a wire path through blood vessels. Generally, each catheter may comprise a catheter body comprising a proximal portion and a distal portion. The catheters may comprise one or more adaptors or handles coupled to the proximal portion, which may be used to help aid in advancement, positioning, and/or control of the catheter within the vasculature, and may further be used to actuate or otherwise advance a guidewire through the catheter body and/or introduce one or more fluids or substances into and/or through the catheter. Additionally, the catheters described here may also generally comprise one or more alignment elements configured to align with the one or more alignment elements of another catheter. Some of the catheters described here may also generally comprise a side aperture (i.e., a port on the side of the catheter body), a deflection surface, which may or may not be part of a deflector, and one or more alignment elements configured to align with the one or more alignment elements of another catheter.

The catheters may additionally comprise one or more lumens or passageways extending at least partially along or through the catheter that may be used to pass one or more wires, one or more drugs or fluids (e.g., contrast agents, perfusion fluids), combinations thereof, or the like at least partially along or through the catheter. The distal tip of the catheter may be configured to aid in advancement of the catheter and/or to be atraumatic. In some variations, the tip may comprise one or more rapid exchange portions or other lumens for advancement of the catheter over a guidewire.

I. Systems

Described here are systems for positioning a wire for advancement through a vessel wall and advancing the wire through the vessel wall, and for bypassing an occlusion or other barrier within an endoluminal space. The systems described here may generally comprise a plurality of catheters that may each comprise a catheter body having a lumen therethrough, one or more ports for passage of a wire (e.g., a guidewire) therethrough, one or more deflection surfaces to modify the path of the wire and position it appropriately to traverse the vessel wall and, in some embodiments, enter another catheter, and one or more alignment elements to assist in aligning the catheters to create a pathway through the vessels or around an occlusion. The systems described here may also comprise one or more guidewires, instructions for using the system, and/or tools for completing a procedure after guidewire placement, for example, stents or stent grafts, balloons (including cutting balloons), cutting, punching, or coring tools, and/or ablating devices, a combination thereof, and the like.

In some embodiments the systems described here may comprise a first catheter comprising one or more magnetic alignment elements that may be advanced into a first vessel and a second catheter comprising one or more magnetic alignment elements that may be advanced into a second vessel. The one or more magnetic alignment elements on the first and second catheters may interact to bring the first and second catheters and the first and second vessels closer together. In some variations, the one or more magnetic alignment elements may interact to rotationally and/or axially align the first and second catheters. For example, in some instances, the one or more magnetic alignment elements may align the first and second catheters such that a guidewire advanced through a side aperture on the first catheter may directly contact the first vessel wall and may automatically be directed toward the second vessel, which may decrease or minimize the distance that the guidewire must travel from the first vessel to the second vessel.

A. Two Catheter System

As mentioned above, the systems described here may comprise a first catheter for advancement within a vessel lumen to a first side of a first target location and a second catheter for advancement outside of the vessel lumen to a second target location. In some variations, the second target location may be on the second, opposite side, of the first target location. In some embodiments, the first catheter may be a delivery catheter and the second catheter may be an alignment catheter. A delivery catheter, as will be described in detail below, may be used to advance a wire therethrough and deliver the wire to a target location, while an alignment catheter, as will also be described below, may be used to assist in positioning the first catheter in the desired location to pierce one or more vessels (e.g., it may comprise one or more alignment elements), but it may not be configured to receive the wire therethrough. In other variations, the first catheter may be a delivery catheter, while the second catheter may be a receiving catheter. A receiving catheter may be used to both assist in aligning or positioning the catheters relative to one another and the vessels, and may also receive the wire after the wire pierces the vessel wall(s). In some variations, the two catheter system described here may comprise one or more wires.

Figure 1B:
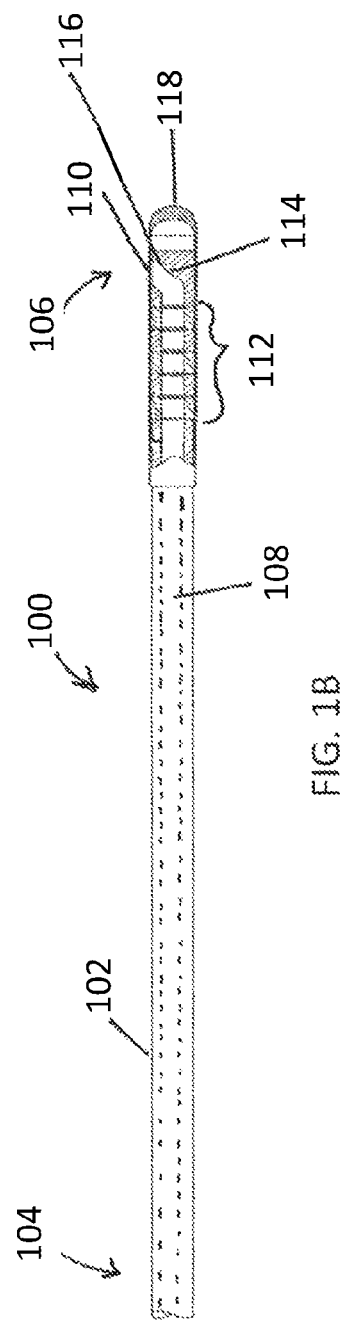
FIG. 1B depicts a partially transparent view of the catheter shown in FIG. 1A.

FIGS. 1A and 1B depict an illustrative variation of a catheter suitable for use as a delivery catheter, alignment catheter, or receiving catheter. Specifically, FIG. 1A depicts a top view of a catheter (100) comprising a catheter body (102) comprising a lumen (108) therethrough, a proximal portion (104), and a distal portion (106). FIG. 1B depicts the catheter (100) with the distal portion (106) of the catheter body (102) illustrated as partially transparent. The distal portion (106) of the catheter (100) may comprise a port or side aperture (110), one or more alignment elements (112), and a deflector (114). In some variations, the distal portion (106) of the catheter body (102) may also comprise a cap (118) coupled to the proximal portion (104) of the catheter body (102), however, it need not. It should be appreciated that the lumen (108) may or may not extend the full length of the catheter. Additionally, in some variations, the cap (118) may be atraumatic and/or the catheter (100) may comprise an atraumatic tip to prevent damage to surrounding tissue during advancement of the catheter through the vasculature.

The port (110) may be located along the length of the catheter body (102) (i.e., on the side of the catheter body (102)) and may be sized and configured to allow passage of a wire therethrough. The port (110) may be fluidly coupled to the lumen (108) such that a wire or another element may be advanced from the proximal portion (104) of the catheter body (102) through the lumen (108) to and through the port (110), to a location outside the catheter body (102). In some variations, the port (110) may be covered with a thin membrane that may assist in maintaining the sterility of the catheter and/or may prevent the lumen from becoming clogged. The membrane may be pierced by the wire in use to allow passage of the wire therethrough, or may be otherwise removed before or during use of the catheter (100). While depicted as circular, the port may have any suitable shape, including oval, square, and the like. In variations in which multiple catheters are used, the port (110) on each catheter may have the same size and shape, or the ports (110) on the catheters may differ. The ports (110) may have any suitable size. For example, in some variations, the ports (110) may be relatively small, e.g., have a 0.127 mm (0.005 inch) diameter, width, or length, while in other variations, the ports (110) may be relatively large, e.g., have a 7.62 cm (3.00 inch) diameter, width, or length. In some variations, the port (110) on the delivery catheter may be smaller (i.e., have a smaller diameter, width, or length), than the port (110) on the receiving catheter. Utilizing a smaller port (110) on the delivery catheter and a larger port (110) on the receiving catheter may assist in positioning the wire to puncture and traverse the vessel wall(s) and may make it easier for the wire to be advanced through the port (110) and into the lumen (108) of the receiving catheter. It should be appreciated that in variations in which an alignment catheter is used, the alignment catheter may not have a port (110).

Figure 11A:
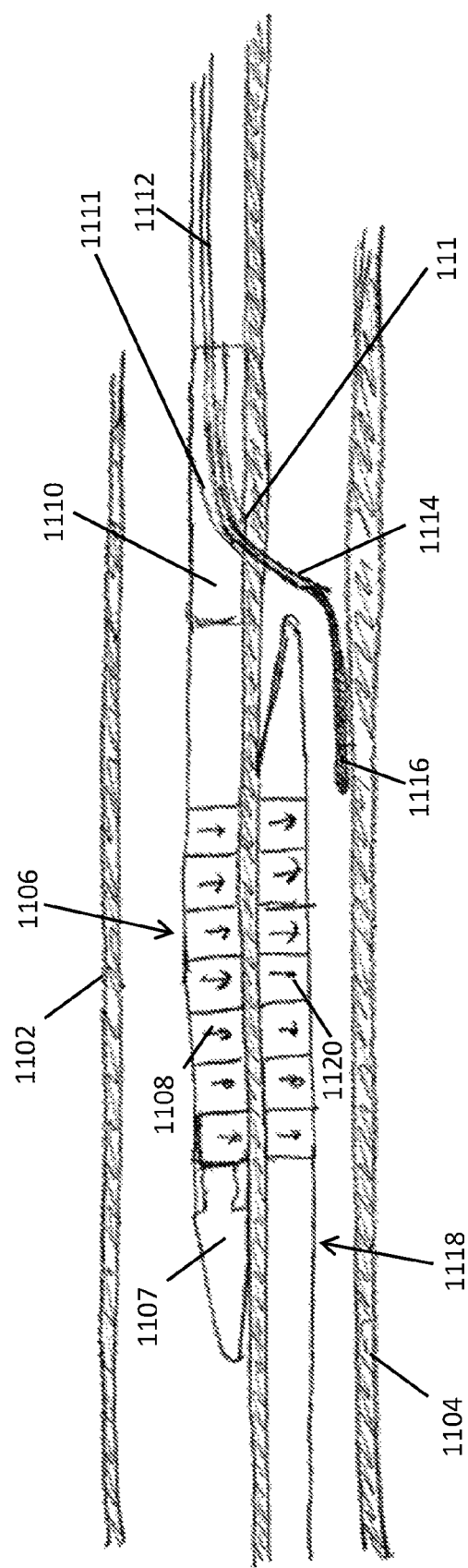
FIGS. 11A-11B depict a variation of a method for advancing a guidewire and a needle between two vessels.

As mentioned above, the distal portion (106) may comprise a deflector (114) comprising an inclined deflection surface (116) that may alter the direction the wire is traveling and may guide the wire from the lumen (108) to the port (110) or vice versa, depending on whether the catheter is delivering or receiving the wire. In some variations the catheters described herein the deflection surface may be straight or linear as depicted in FIG. 1A, while in other variations it may be curved, as depicted in FIG. 11A. Additionally, in delivery catheters, the deflection surface (116) may also assist in positioning the wire to facilitate piercing the vessel wall(s). As shown here, the deflector (114) may be positioned at the distal end of the lumen (108) with the deflection surface (116) positioned toward the proximal portion (104) of the catheter body (102). The deflection surface (116) may comprise a positive slope (i.e., increasing from a proximal end to a distal end of the catheter, as depicted in FIG. 1B) or a negative slope (i.e., decreasing from a proximal end to a distal end of the catheter), depending on the orientation of the catheters with respect to each other and/or the vessel wall(s) intended for puncture. In some variations in which delivery and receiving catheters are used, the delivery and receiving catheters may be arranged such that the deflection surface (116) in the delivery catheter may comprise a positive slope, while the deflection surface (116) in the receiving catheter may comprise a negative slope or vice versa. In some variations, when not in use, the deflection surfaces of the delivery and receiving catheters may each comprise slopes with the same sign (e.g., both positive). The slopes of the deflection surfaces (116) of the delivery and receiving catheters may facilitate the transition of the wire from the delivery catheter to the receiving catheter. For example, in some variations, the slope of the deflection surface (116) in the delivery catheter may have a greater magnitude than the slope of the deflection surface (116) in the receiving catheter. In other variations, the magnitudes of the slopes of the deflection surfaces (116) in the delivery and receiving catheters may be the same. It should be appreciated that in some variations, the deflector and/or deflection surface may be integrally formed with catheter. For example, the deflector and/or the deflection surface may be formed from a wall of the lumen of the catheter (e.g., a distal portion of the lumen may curve or angle). Put another way, the deflector and/or the deflection surface need not be a separate element.

The deflection surface (116) in a delivery catheter may comprise a slope that results in an exit angle (i.e., the angle formed between the wire and the catheter body (102) adjacent to the port (110) as the wire exits the catheter body (102) through the port (110), as depicted in FIG. 2B) between about 20 degrees and about 90 degrees. More specifically, the deflection surface (116) may comprise a slope that results in an exit angle of about 30 degrees, about 40 degrees, about 50 degrees, about 60 degrees, about 70 degrees, or about 80 degrees. As discussed in more detail below, in embodiments in which the wire enters a receiving catheter after piercing one or more vessel walls, the slope of the deflection surface (116) may also assist in positioning the wire with respect to the receiving catheter to facilitate entrance into the receiving catheter.

In some variations, the deflector may further comprise a housing comprising an aperture that may be sized and/or shaped to correspond with the port in the catheter. In these variations, the deflector may comprise a shape (e.g., cylindrical) sized to fit securely within the lumen of the catheter and may have a lumen in a proximal portion that leads to the deflection surface in a distal portion. In these variations, the deflector may be positioned within the lumen of the catheter and coupled to the catheter such that the aperture in the housing aligns with the port in the catheter to allow passage of a wire through both the aperture in the deflector and the port in catheter.

As mentioned above, the distal portion (106) of catheter (100) may comprise one or more (e.g., two, three, four, five, six, seven, eight, or more) alignment elements (112) that may assist in aligning or otherwise repositioning the catheter (s) within the vasculature. For example, in some instances, the alignment elements may help bring two or more catheters (and with them, two or more blood vessels) in closer approximation. In other instances, the alignment elements may help ensure that one or more catheters are in proper axial and/or rotational alignment relative to another catheter. Ensuring proper position of the catheters and blood vessels may help facilitate advancement of the wire through one or more blood vessel walls. In some variations, catheters may comprise mechanical alignment elements, such as protrusions, grooves, flat surfaces, and the like, that may or may not interact with one or more alignment elements on another catheter. Additionally or alternatively, a catheter may comprise magnetic alignment elements, i.e., one or more magnetic components that may interact with one or more magnetic components of another catheter. In still other variations, the catheter may comprise visual alignment elements, for example, one or more markers that may help a user to align one or more catheters. It should be appreciated that each of the catheters described here may comprise any alignment element or combination of alignment elements described.

In variations in which magnetic alignment elements are used, the magnetic alignment elements may be attracted to one or more additional elements (e.g., one or more portions of a second catheter) to help position or align the catheter within a vessel. For example, a catheter may comprise one or more magnetic alignment elements that act to attract the catheter toward one or more portions of another catheter, thereby bringing the catheters in closer approximation, rotationally and/or axially orienting the catheters, and/or mating a surface of the catheter with one or more surfaces or portions of another catheter.

A magnetic alignment element may comprise any suitable magnet or magnetic material. For example, in some variations, a catheter may comprise one or more rare-earth magnets (e.g., neodymium magnets or samarium-cobalt magnets) and/or one or more selectively-activated electromagnets. In variations where a catheter comprises a plurality of magnets, these magnets may be grouped into one or more arrays. These magnetic arrays may be located inside or outside of a catheter (or a combination thereof), and may be positioned anywhere along the length of the catheter. When two or more catheters comprise magnets or magnet arrays, each magnet or magnet array may be configured or arranged to align with one or more magnets or magnet arrays from another catheter. Each magnet may be fixed in or on a catheter by any suitable method. For example, in some variations one or more magnets may be embedded in, adhered to, or friction fit within a catheter. Each magnet may have any suitable diameter (or for non-circular cross-sections, height and/or width) (e.g., from about 0.25 mm (0.010 inches) to about 8 mm (0.315 inches)) or length (e.g., from about 0.25 mm (0.001 inches) to about 25 mm (0.984 inches)). In some variations, each magnet may have a diameter (or for non-circular cross-sections, height and/or width) of about 1.91 mm (0.075 in.), about 2.03 mm (0.080 in.), about 2.34 mm (0.092 in.), about 2.79 mm (0.110 in.) or the like or length of about 5 mm (0.197 in.), about 10 mm (0.394 in.), about 15 mm (0.591 in.), about 20 mm (0.787 in.), or the like, and may be separated from adjoining magnets by any suitable distance (e.g., about 1 mm (0.039 in.), about 5 mm (0.197 in.), and the like). Magnet size may generally be directly proportional to catheter size (i.e., magnet size may increase with increasing catheter size). In some variations, the magnets of an array may have alternating polarity (e.g., each magnet will have the opposite polarity as any adjacent magnets), matching polarity, or combinations thereof. In other variations, one or more portions of the catheter may be made from a magnetic material, and/or may be embedded with one or more magnetic particles/materials. Each magnet may have any suitable shape for placement inside or outside of the catheter. Magnets may be cylindrical, semi-cylindrical, tube-shaped, box-shaped, or the like. In some variations, the magnetic alignment elements may comprise Halbach arrays or focused magnets, as described in more detail in U.S. patent application Ser. No. 14/214,503, filed Mar. 14, 2014, and titled "FISTULA FORMULATION DEVICES AND METHODS THEREFOR," and/or in U.S. patent application Ser. No. 14/657,997, filed Mar. 13, 2015, and titled "FISTULA FORMATION DEVICES AND METHODS THEREFOR," the contents of each of which are hereby incorporated by reference in their entirety.

The catheter body (102) may comprise any suitable cross-sectional shape. In some variations, the catheter body may comprise a circular cross-sectional shape (as shown in FIGS. 1A and 1B), a square cross-sectional shape (as shown in FIG. 3A), a rectangular cross-sectional shape, a combination thereof, or the like. For example, in some instances, the catheter body may have a first cross-sectional shape in a proximal portion (e.g., circular), and a second cross-sectional shape in a distal portion (e.g., square) or in the portion comprising the one or more alignment elements (if different from the distal portion). For example, it may be desirable to utilize a catheter body comprising a square cross-sectional shape in the portion comprising the one or more alignment elements such that the catheter(s) comprises a flat alignment surface. In variations in which the alignment element comprises a magnet, the flat magnetic surface allows lateral magnetic coaption force to be generated and translated into an aligning torque, thereby more easily rotating and aligning the catheters. Additionally, the use of a flat alignment surface may bring the catheters closer together, compress the intervening vessel wall(s) more, and create a larger flat area between the two catheters, all of which may make puncturing and advancing the wire through vessel wall(s), and optionally into another catheter, easier.

In some instances, it may be desirable to utilize a wire to assist in advancing the catheters described here to a target tissue within the vasculature. Accordingly, in some variations, the catheters described here may be configured to both advance through the vasculature along a guidewire and deliver or receive a wire that may be used in fistula formation. For example, FIGS. 3A and 3B depict a perspective view and an illustrative cross-sectional view of such a variation of a catheter (300). As shown there, the catheter (300) may comprise a catheter body (302), a deflector (304) comprising a deflection surface (306), a first alignment element (308), a second alignment element (312), a port (310), and a distal opening (316). In this variation, the catheter body (302) may comprise a first lumen (314) therethrough, similar to the lumen (108) described above with respect to FIGS. 1A and 1B, and a second lumen (318) therethrough that may fluidly couple a proximal opening (not depicted) in a handle or a proximal portion of the catheter body (302) and the distal opening (316). The first and second alignment elements (308, 312) and the deflector (304) may be positioned within the first lumen (314) and a guidewire (320) may be positioned within the second lumen (318). While catheter (300) is depicted with a discrete deflector (304), in some variations, the deflection surface (306) may be formed from a wall of the catheter (300).

While the catheter (300) is depicted with a first lumen (314) and a second lumen (318), it should be appreciated that in other variations, the catheter (300) may comprise a single lumen that may be utilized for both a guidewire to assist in advancing the catheter through the vasculature, and a wire that may be used to connect vessels. For example, in this embodiment, a single lumen may fluidly couple a proximal opening, a distal opening, and a port, and the one or more alignment element(s) and deflector may be sized, shaped, and positioned within the lumen such that a guidewire may pass through the lumen underneath or next to the alignment element(s) and the deflector. For example, the alignment element(s) may be smaller (e.g., comprise a smaller diameter, height, volume) than the diameter of the lumen of the catheter and may be positioned such that a wire may pass around or next to the alignment element(s) (e.g., may be positioned against an internal surface of the catheter at the top, bottom, or on either side of the lumen and/or be embedded within a catheter wall). In other embodiments, the catheter may comprise a single lumen and the one or more alignment element(s) and deflector may comprise a lumen therethrough to accommodate passage of the guidewire through the catheter to the distal opening. In still other embodiments in which the catheter comprises a single lumen, the catheter may comprise a combination of elements sized, shaped, and/or positioned to allow passage of the guidewire underneath or around the elements and elements comprising a lumen therethrough to allow passage of the guidewire therethrough. For example, the alignment elements may be sized, shaped, and/or positioned within the lumen such that the guidewire may pass underneath or next to the alignment elements, while the deflector may comprise a lumen therethrough so that the guidewire may pass through the deflector, or vice versa.

Figure 4A:
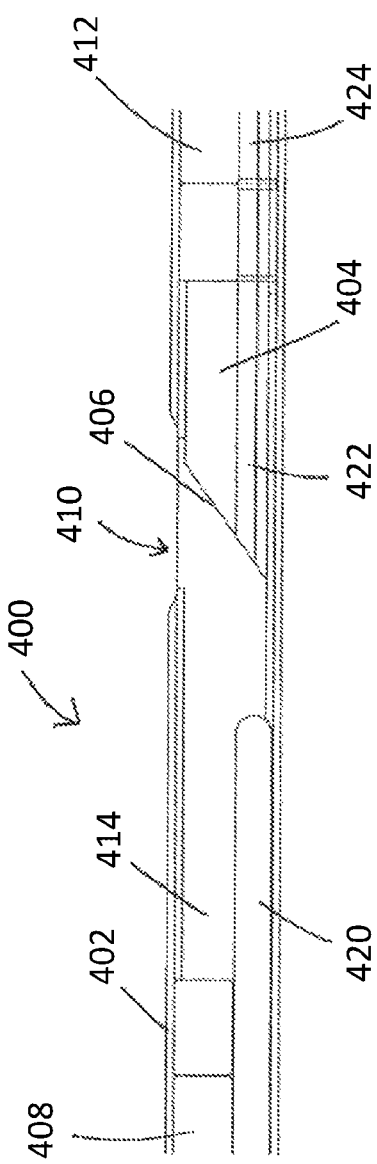
FIGS. 4A and 4B illustrate side cross-sectional and perspective cross-sectional views, respectively, of a variation of a catheter.
Figure 4B:
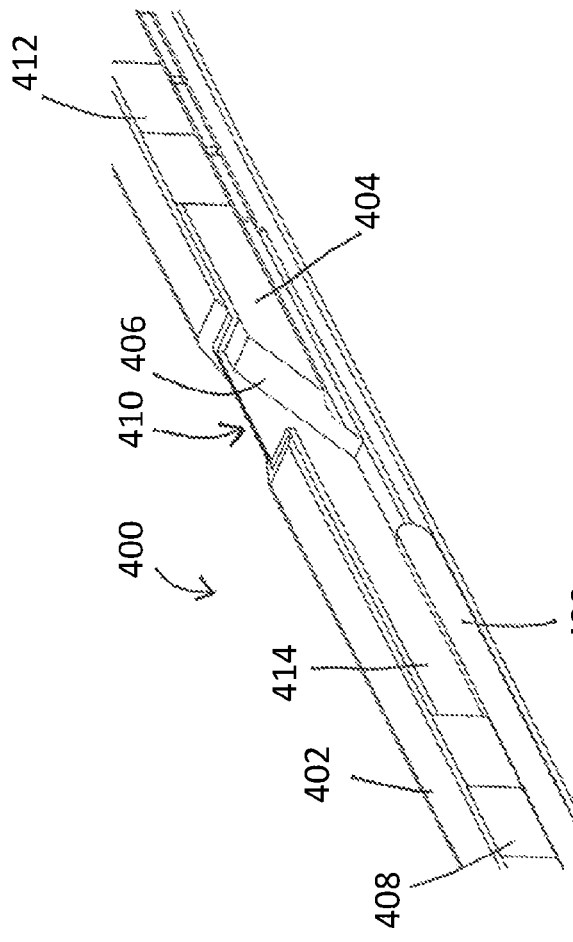
Figure 4C:
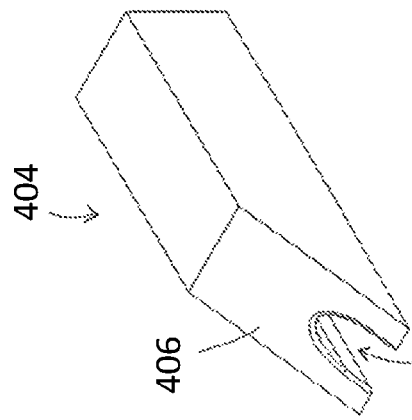
FIG. 4C depicts a perspective view of a deflector.

In some variations, the catheter may comprise a single lumen that may be utilized for both a guidewire for advancing the catheter through the vasculature and a guidewire that may be used to connect two vessels. For example, FIGS. 4A and 4B depict a cross-sectional view and a perspective cross-sectional view, respectively, of a variation of a catheter (400) comprising a catheter body (402) comprising a single lumen (414) therethrough, a deflector (404) comprising a deflection surface (406), a first alignment element (408), a second alignment element (412), a port (410), and a distal opening (not shown). The deflector (404) and the alignment elements (408, 412) may be configured such that a guidewire may pass through the catheter, such as by passing around or through the deflector (404) and the alignment elements (408, 412). In the variation shown in FIGS. 4A and 4B, the first alignment element (408) may be sized and positioned within the lumen (414) such that a guidewire (420) may pass underneath or next to it, while the deflector (404) and the second alignment element (412) may each comprise a lumen or opening (422, 424, respectively) through which the guidewire (420) may travel to reach the distal opening. For additional clarity, FIG. 4C depicts the deflector (404) shown in FIGS. 4A and 4B removed from the catheter (400). While depicted in FIG. 4C as a separate element, in some variations the deflector (404) and/or the deflection surface (406) may be formed from a wall of the catheter (400).

1. Delivery Catheter

FIGS. 2A and 2B depict an illustrative cross-sectional view of a variation of a delivery catheter as a wire is advanced in the direction of the arrow (e.g., from a proximal to a distal end of the catheter) through a lumen of the catheter (FIG. 2A) and out a port in the catheter body (FIG. 2B). As shown there, the delivery catheter (200) may comprise a catheter body (202) comprising a lumen therethrough (214), a deflector (204) comprising a deflection surface (206), a first alignment element (208), a second alignment element (212), and a port (210). The first alignment element (210) is located proximal to the port (210) and the deflector (204), while the second alignment element (212) is located distal to the port (210) and the deflector (204). Put another way, the deflector (204) is located between the first alignment element (208) and the second alignment element (212). In the embodiment shown in FIGS. 2A and 2B, the first and second alignment elements (208, 212) comprise magnetic arrays that are positioned within the lumen (214) of the catheter body (202), however, as described above, this need not be the case. The alignment elements (208, 212) may comprise any of the alignment elements described above. The first alignment element (208) may comprise a lumen therethrough to accommodate passage of a wire (216) through the alignment element (208), as shown. Moreover, while the deflector (204) is depicted as a separate element, it need not be, and in some variations, the deflector (204) and the deflection surface (206) may be formed from a wall of the catheter.

In use, the wire (216) may be advanced from a proximal end of the catheter (200) toward the deflector (204) and the distal end of the catheter, as shown by the arrow, such that the wire (216) may contact the deflection surface (206) of the deflector (204). The deflection surface (206) may prevent the wire (216) from advancing any further distally, and may alter its path so that the wire (216) exits the lumen (214) through the port (210) at an exit angle (218), as described above. The wire (216) may then be advanced through the vessel wall(s) and, optionally, into a receiving catheter. While the wire (216) is depicted with a rounded distal tip (220), this need not be the case. In some variations, the wire (216) may comprise a distal tip (220) that is configured to pierce or create an opening in tissue (e.g., a sharpened distal tip or the like). In some instances, the wire (216) may comprise a distal tip (220) that is bent, which may aid in redirection of the wire.

2. Receiving Catheter

FIGS. 5A and 5B depict cross-sectional and perspective cross-sectional views, respectively, of a receiving catheter. As shown there, a receiving catheter (500) may comprise a catheter body (502) comprising a lumen therethrough, a deflector (504) comprising a deflection surface (506), a port (510), a first alignment element (508), a second alignment element (512), and a guide funnel or funneling element (516). In this variation, the first alignment element (508) may comprise a lumen (518) therethrough for passage of a wire after it enters the catheter body (502) through the port (510) and is redirected by the deflection surface (506) of the deflector (504) into the funneling element (516) and then into the first alignment element (508). In some variations, the deflector (504), the deflection surface (506), and/or the funneling element (516) may be formed from a wall of the catheter (e.g., may be part of the catheter body).

The funneling element (516) may be used to direct the distal tip of the wire into the lumen (518) of the first alignment element (508) once it is deflected by the deflection surface (506). Additionally, the funneling element (516) may fluidly couple the deflector (504) and the first alignment element (508). The funneling element (516) may comprise a cone-shaped or frustoconical body comprising a lumen. The lumen may have a first smaller diameter at a proximal end of the funneling element (516) and a second larger diameter at a distal end of the funneling element (516), such that the lumen has a proximally decreasing diameter. In some variations, the lumens of the funneling element (516) and the first alignment element (508) may be the same size and shape and/or the funneling element (516) and the first alignment element (508) may be positioned such that their lumens align. The funneling element (516) may or may not be directly adjacent to the first alignment element (508). In some variations, and the first alignment element (508) may, instead of comprising a lumen therethrough, be sized, shaped, and positioned to allow passage of the wire underneath or next to the first alignment element (508) through the lumen of the catheter body (502). In these variations, the funneling element (516) may fluidly couple the deflector (504) to the portion of the catheter lumen proximal to the funneling element (516). In some variations, the receiving catheter may not comprise a guide funnel or funneling element.

3. Use of Delivery and Receiving Catheters

As mentioned above, the delivery and receiving catheters described here may be configured to align with each other, or to otherwise influence the position of one another. For example, FIGS. 6A and 6B depict side cross-sectional and top perspective cross-sectional views, respectively, of a system (600) comprising a delivery catheter (602) and a receiving catheter (650) in use with a wire (620) (vessel wall(s) have been omitted for clarity). As shown there, the delivery catheter (602) may comprise a catheter body (616) comprising a lumen (614) therethrough, a deflector (604) comprising a deflection surface (606), a first alignment element (608) comprising a lumen (618) therethrough, a port (610), and a second alignment element (612). The receiving catheter (650) may comprise a catheter body (652), a deflector (654) comprising a deflection surface (656), a first alignment element (658) comprising a lumen (664) therethrough, a port (660), a funneling element (666), and a second alignment element (662). As mentioned above, in some variations, the deflectors, the deflection surfaces, and/or the funneling element may be formed integrally with the catheter body.

The system may also comprise a wire (620) that may be used to puncture the vessel wall(s). In some variations, the wire (620) may comprise a distal tip configured to puncture or otherwise form a hole in tissue. In some instances, the wire (620) may be a guidewire. In variations in which the delivery catheter (602) and/or the receiving catheter (650) may be configured to advance through the vasculature to a target location utilizing a guidewire, the system may comprise a first guidewire for advancing either of the delivery or receiving catheters to the target location, and a second wire (620) to puncture the vessel wall(s). In yet other variations, the same wire (620) may be used to both advance the delivery catheter to the target location and to puncture the vessel wall(s). In still other variations, the system may comprise a first guidewire for advancing the delivery catheter to a target location, a second guidewire for advancing the receiving catheter to a corresponding target location, and a third wire (620) to puncture the vessel wall(s).

In use, the delivery catheter (602) and the receiving catheter (650) may be advanced through the vasculature to corresponding target locations in a first vessel and a second vessel or cavity, respectively. Once the delivery catheter (602) and the receiving catheter (650) are located near each other, the alignment elements of the catheters may be used to align the catheters axially and/or rotationally. In some variations, the delivery catheter (602) and the receiving catheter (650) may be configured to be axially aligned in an antiparallel configuration. For example, the first alignment element (608) on the delivery catheter (602) may be configured to mate with, attract, or otherwise interact with the second alignment element (662) on the receiving catheter (650), while the second alignment element (612) on the delivery catheter (602) may be configured to mate with, attract, or otherwise interact with the first alignment element (658) on the receiving catheter (650) to form a wire or guidewire pathway through the delivery and receiving catheters (602, 650). In other variations, the delivery catheter (602) and the receiving catheter (650) may be configured to be axially aligned in a parallel configuration. For example, the first alignment element on the delivery catheter may be configured to mate with, attract, or otherwise interact with the first alignment element on the receiving catheter, and the second alignment element on the delivery catheter may be configured to mate with, attract, or otherwise interact with the second alignment element on the receiving catheter. In some variations, the delivery catheter (602) and the receiving catheter (650) may be configured such that they may be aligned in either parallel or antiparallel configurations.

Additionally, the delivery catheter (602) and the receiving catheter (650) (e.g., the alignment elements) may be configured to align the delivery and receiving catheters lengthwise, as opposed to at the distal ends of the catheters. In variations in which an alignment catheter is used instead of a receiving catheter (i.e., in which the wire (620) is not advanced into another catheter after exiting the delivery catheter), the alignment catheter may comprise any of the alignment element configurations described with respect to the receiving catheter. Moreover, while the alignment elements are depicted as magnetic arrays, it should be appreciated that they may be any of the alignment elements described above. Additionally, while both the delivery and receiving catheters (602, 650) are each depicted with two alignment elements, they may comprise any suitable number of alignment elements, as described above.

Once the delivery and receiving catheters (602, 650) are aligned, they may be configured such that the wire may be advanced out of the delivery catheter, through one or more vessel walls, and into the receiving catheter. More specifically, the wire (620) may be advanced from a proximal end of the delivery catheter (602) through the lumen (614) in the delivery catheter body (616) and the lumen (618) in the first alignment element (608) in the delivery catheter (602), to the deflection surface (606) on the deflector (604). The deflection surface (606) may then alter the direction of the wire (620) such that it exits the delivery catheter (602) through the port (610) at an appropriate exit angle to both puncture the vessel wall and subsequently enter the port (660) of the receiving catheter (650). After the wire (620) punctures one or more vessel walls, it may enter the receiving catheter (650) through the port (660). As the wire (620) is continued to be advanced, it may reach the deflection surface (656) of the deflector (654), which may then alter the direction of the wire (620) such that it enters the funneling element (666), and the lumen (664) of the first alignment element (658) in the receiving catheter (650). As mentioned above, the deflection surfaces (606, 656) of the deflectors (604, 654) in both the delivery and receiving catheters (602, 650) may be configured to facilitate the transition of the wire (620) from the delivery catheter (602) to the receiving catheter (650) and guide the wire (620) from the delivery catheter lumen (614) to a lumen in the receiving catheter (650).

B. Three Catheter System

As mentioned above, the systems described herein may be used to bypass an occluded vessel. These systems may comprise a first catheter for advancement within an occluded vessel lumen to a first side of an occlusion, a second catheter for advancement outside of the occluded vessel to a location at or near the occlusion, and a third catheter for advancement within the occluded vessel lumen to a second, opposite side of the occlusion. In some variations, the first catheter may be any of the delivery catheters described above, and the third catheter may be any of the receiving catheters described above. The second catheter may be a bypass catheter that is used to both receive and deliver a wire in order to advance the wire outside of the first vessel around the occlusion. For example, the second catheter may be configured to receive a wire after it is deployed from the delivery catheter through a vessel wall(s), house or otherwise transport the wire to avoid or bypass the occlusion in the occluded vessel, and deliver the wire to a receiving catheter within the occluded vessel on the opposite side of the occlusion.

FIGS. 7A and 7B depict an illustrative variation of a catheter suitable for use as a bypass catheter. Specifically, FIG. 7A depicts a top view of a catheter (700) comprising a catheter body (702) comprising a lumen (708) therethrough, a proximal portion (704), and a distal portion (706). FIG. 7B depicts a view of the catheter (700) with the distal portion (706) of the catheter body (702) illustrated as partially transparent. The distal portion (706) of the catheter (700) may comprise a first port or side aperture (710), a second port or side aperture (712), a first alignment element (714), a second alignment element (716), a first deflector (718), and a second deflector (720). In some variations, the catheter body may circumferentially surround the lumen (708) between the first and second ports (710, 712). In some of these variations, the catheter (700) may further comprise a slit (722) between the first and second ports (710, 712) through which the wire may pass to exit the catheter body (702) after it has entered the receiving catheter, as will be explained in more detail below. In some variations, the distal portion (706) of the catheter body (702) may also comprise a cap (724) coupled to the proximal portion (704) of the catheter body (102), however, it need not. It should be appreciated that the lumen (708) may or may not extend the full length of the catheter (700). Additionally, in some variations, the cap (724) may comprise an atraumatic tip and/or the catheter (7000) may comprise an atraumatic tip to prevent damage to surrounding tissue during advancement of the catheter through the vasculature.

The bypass catheter may comprise elements that are similar to elements described above with respect to the delivery and receiving catheters. For example, the catheter body (702), the ports (710, 712) and the first and second alignment elements (714, 716), may have any of the configurations previously described with respect to those elements in the delivery and/or receiving catheters. For example, the first port (710) may have any of the configurations described above with respect the receiving catheters, and the second port (712) may have any of the configurations described above with respect to the delivery catheters, or vice versa.

While many of the components of the bypass catheter may be similar to or the same as components described above with respect to the delivery and receiving catheters, the bypass catheter differs in that it may comprise a first deflector (718) comprising a deflection surface (726) with a positive slope and a second deflector (720) comprising a deflection surface (728) with a negative slope (or vice versa, depending on catheter and/or vessel orientation). Put another way, the first and second deflectors (718, 720) may comprise deflection surfaces (726,728) with slopes having opposite signs. This is because the first and second deflectors (718, 720) may be configured to serve different purposes; one may be configured to modify the direction of the wire just after it is received through one of the ports, and the other may be configured to modify the direction and angle of the wire to position it to puncture tissue and be received by a receiving catheter.

Turning back to FIG. 7B, in the embodiment shown there, the first deflector (718) may comprise a deflection surface (726) with a positive slope that is configured to alter the path of the wire so that it travels through the lumen (708) of the catheter body (702) toward the second deflector (720), while the second deflector (720) may comprise a deflection surface (728) with a negative slope that is configured to alter the path of the wire so that it travels through the second port (712) and into the port on the receiving catheter. The deflection surface (728) of the second deflector (720) may also be selected to appropriately position the wire to pierce the vessel wall(s). The first deflector (726) may comprise any of the deflectors described above with respect to the receiving catheter. Similarly, the second deflector (720) may comprise any of the deflectors described above with respect to the delivery catheter. In some variations, the first and second deflectors (718, 720) may be connected by a deflector housing such that the bypass catheter comprises a single deflector comprising two deflection surfaces (e.g., deflection surfaces (726, 728)). Moreover, in some variations, the first and second deflectors (718, 720) and/or the first and second deflection surfaces (726, 728) may be formed from a wall of the catheter.

As mentioned above, the bypass catheters described herein may comprise a catheter body (702) with a lumen (708) in which the first and second alignment elements (714, 716) and the first and second deflectors (718, 720) may be positioned. In some variations, any of the first alignment element (714), second alignment element (716), first deflector (718), or second deflector (720) may optionally comprise a lumen therethrough to allow passage of a guidewire for advancing the bypass catheter through the vasculature to a target location or may be sized and positioned to allow passage of such a guidewire, as is discussed in more detail above. In other variations, and as depicted in FIG. 7B, the first alignment element (714) and the first deflector (718) may be positioned within the lumen (708) such that they may partially or fully block the lumen (708) between the proximal portion (704) of the catheter body (702) and the first port (710), after which the lumen (708) may reopen and remain open for passage of a wire therethrough until the deflection surface (728) of the second deflector (720). In these variations, the catheter body (702) may comprise a slit (722) through which the wire may exit the catheter body (702) after it has passed through the lumen (708), out of the second port (712), and into the receiving catheter so that tools or devices may be advanced along the wire to bypass the occlusion. In some instances, the catheter body (702) may comprise perforations, a weakened body portion configured to tear to release the wire, or the like in place of the slit (722). In yet other variations, the catheter body (702) may comprise a large gap along the length of the catheter that connects the first and second ports (710, 712), which may be used to release the wire in-situ. In yet other embodiments, the catheter body (702) may comprise a large hole (e.g., a semicircular portion of the catheter body may be removed), and the wire may be guided by a track in the first and second deflectors (718,720) and the internal surface of the catheter body (702) that remains, or in instances in which the first and second deflectors (718, 720) are integrally formed, through the integral deflector.

1. Use of Delivery, Receiving, and Bypass Catheters

Figure 8A:
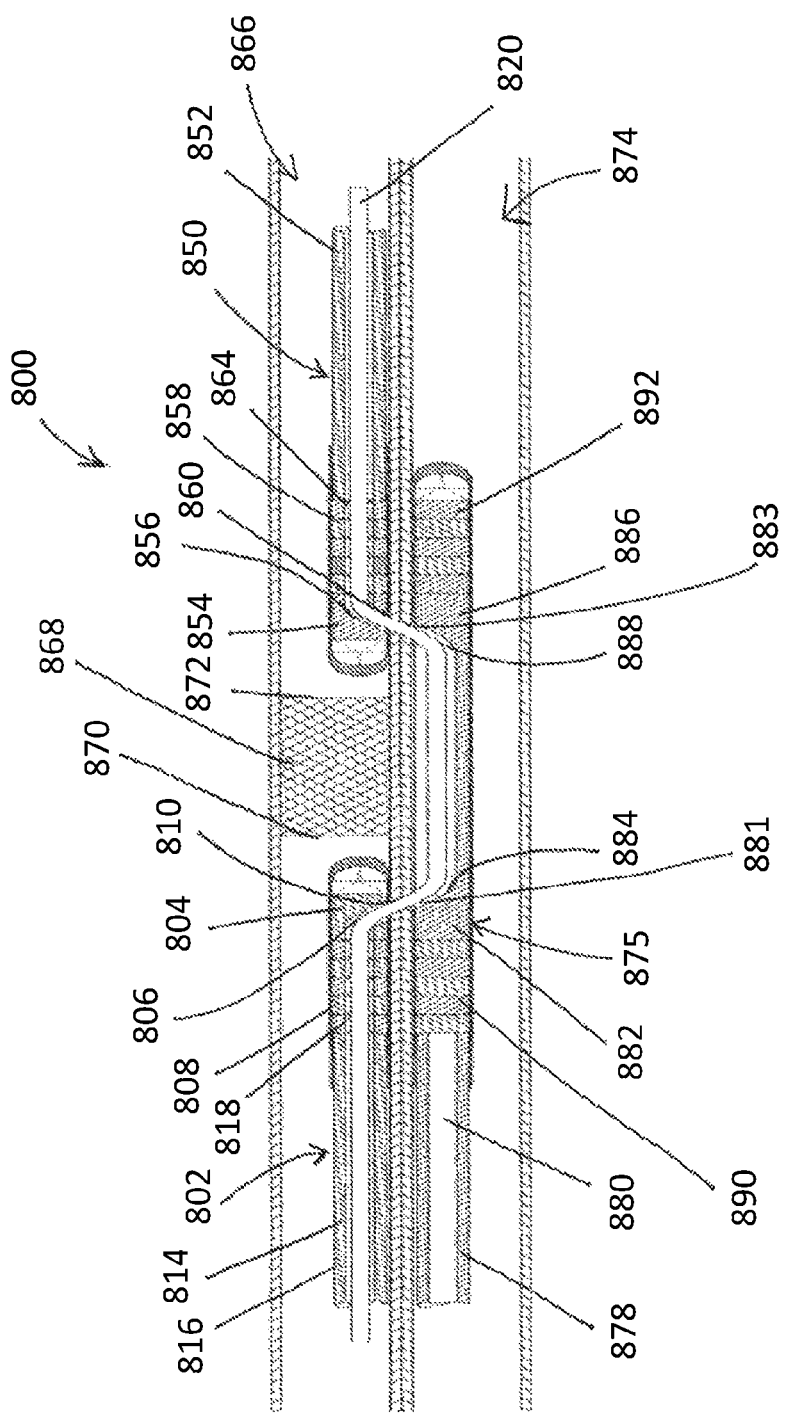
FIGS. 8A and 8B show side cross-sectional and perspective cross-sectional views, respectively, of a variation of a three-catheter system.
Figure 8B:
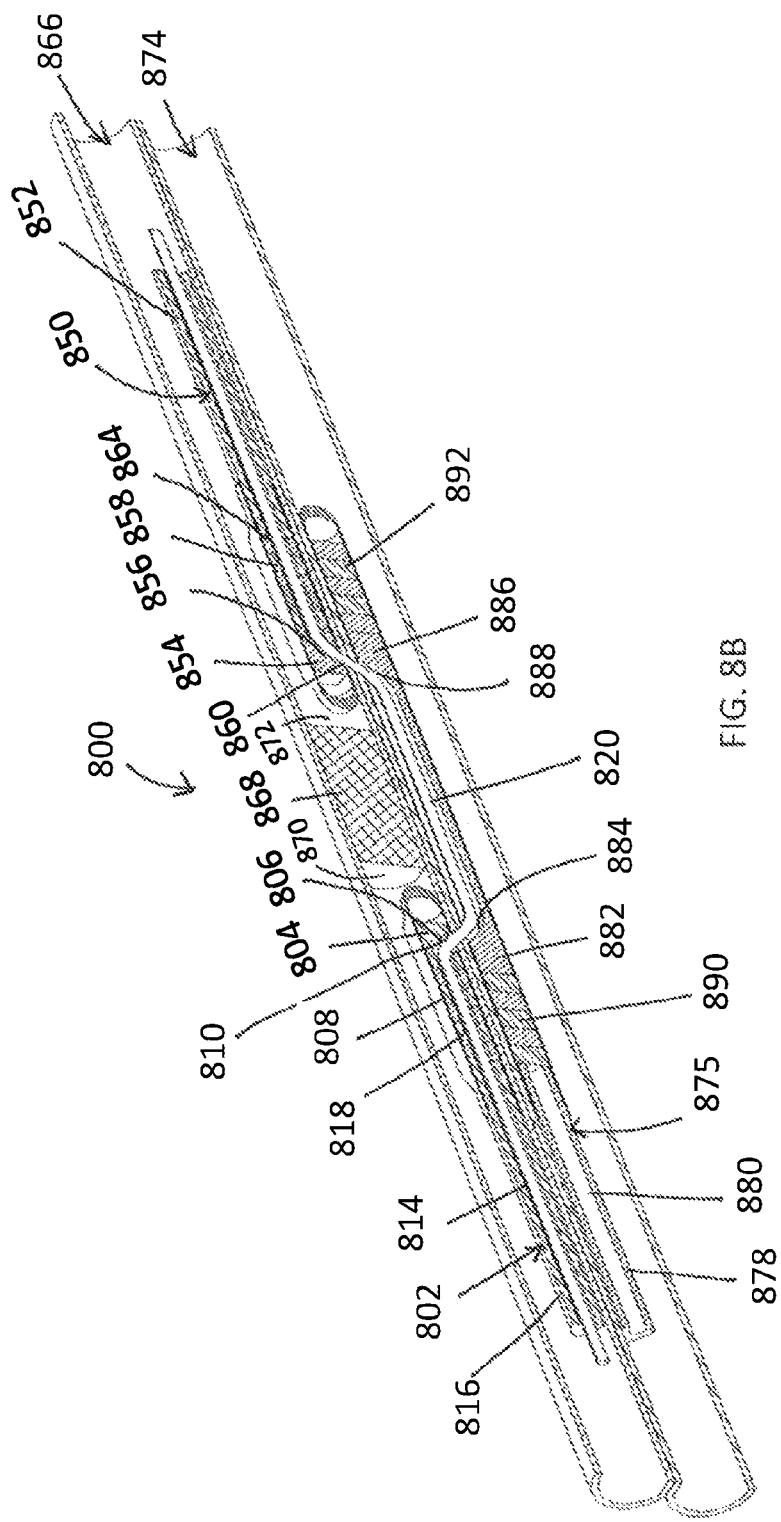

Similarly to the two-catheter system described above, the delivery, bypass, and receiving catheters described here may be configured to align with one another, or to otherwise affect the position of one another. For example, FIGS. 8A and 8B depict side and perspective cross-sectional views, respectively, of a system (800) comprising a delivery catheter (802), a receiving catheter (850), and a bypass catheter (875) in use with a wire (820). The delivery catheter (802) may comprise a catheter body (816) comprising a lumen (814) therethrough, a deflector (804) comprising a deflection surface (806), an alignment element (808) comprising a lumen (818) therethrough, and a port (810). The receiving catheter (850) may comprise a catheter body (852), a deflector (854) comprising a deflection surface (856), an alignment element (858) comprising a lumen (864) therethrough, and a port (860). The bypass catheter (875) may comprise a catheter body (878) comprising a lumen therethrough (880), a first deflector (882) comprising a first deflection surface (884), a second deflector (886) comprising a second deflection surface (888), a first alignment element (890), a second alignment element (892), a first port (881), and a second port (883). As mentioned above, it should be appreciated that the first and second deflectors (882, 886) may be integrally formed or otherwise connected via a deflector housing.

The system may also comprise a wire (820) that may be used to puncture the vessel wall(s). In some variations, the wire (820) may comprise a distal tip configured to puncture or otherwise form a hole in tissue. In some instances, the wire (820) may be a guidewire. In variations in which the delivery catheter (802) and/or the receiving catheter (850) may be configured to advance through the vasculature to a target location utilizing a guidewire, the system may further comprise one or more guidewires for advancing the delivery and/or receiving catheters to the occlusion, and an additional wire (820) to puncture the vessel wall(s) to bypass the occlusion. In some variations, the same wire (820) may be used to both advance the delivery catheter to the target location and to puncture the vessel wall(s).

In use, the delivery catheter (802) may be advanced through the vasculature to a first side (870) of an occlusion (868) in an occluded vessel (866). The receiving catheter (850) may be advanced through the vasculature to a second, opposite side (872) of the occlusion (868) in the occluded vessel (866). The bypass catheter may be advanced through the vasculature to a vessel (874) adjacent to or near the occluded vessel (866) to a location near the occlusion (868).

In some variations, the delivery, receiving, and bypass catheters (802, 850, 875) may be advanced so that the delivery catheter (802) and the bypass catheter (875) are in a parallel orientation and the bypass catheter (875) and the receiving catheter (850) are in an anti-parallel orientation, as depicted in FIG. 8B. Once the delivery catheter (802), the receiving catheter (850), and the bypass catheter (875) are located near each other, the alignment elements of the delivery, receiving, and bypass catheters (802, 850, 875) may be used to align the catheters (802, 850, 875) axially and/or rotationally.

For example, as depicted in FIGS. 8A and 8B, the alignment element (808) on the delivery catheter (802) may be configured to mate with, attract, or otherwise interact with the first alignment element (890) on the bypass catheter (875), while the alignment element (858) on the receiving catheter (850) may be configured to mate with, attract, or otherwise interact with the second alignment element (892) on the bypass catheter (875). This alignment may form a wire or guidewire pathway through the delivery, bypass, and receiving catheters (802, 875, 850).

Once the delivery, bypass, and receiving catheters (802, 875, 850) are aligned, the wire (820) may be advanced out of the delivery catheter, through the vessel walls, into the bypass catheter, back through the vessel walls, and into the receiving catheter to form a guidewire bypass around the occlusion (868). More specifically, the wire (820) may be advanced from a proximal end of the delivery catheter (802) through the lumen (814) in the delivery catheter body (816) and the lumen (818) in the first alignment element (808) in the delivery catheter (802) to the deflection surface (806) on the deflector (804). The deflection surface (806) may then alter the direction of the wire (820) such that it exits the delivery catheter (802) through the port (810) at an appropriate exit angle to puncture both the occluded vessel and non-occluded vessel walls, and subsequently pass through the first port (881) of the bypass catheter (875). After the wire (820) punctures both vessel walls, it may enter the bypass catheter (875) through the first port (881) and be advanced to the first deflection surface (884) of the first deflector (882). The first deflector (882) may then alter the direction of the wire (820) such that it enters the lumen (880) of the bypass catheter (875). The wire (820) may then be advanced through the lumen (880) of the bypass catheter (875) at the location of the occlusion (868) toward the second deflection surface (888) of the second deflector (886), which may alter the direction of the wire (820) again so that it is positioned to exit the bypass catheter (875) through the second port (883). After exiting the bypass catheter (875) through the second port (883), the wire (820) may pierce both the clear and occluded vessel walls, and pass through the port (860) of the receiving catheter (850). Once the wire (820) is advanced through the vessel walls and the into the receiving catheter (850), the deflection surface (856) of the deflector (854) may modify the path of the wire so that it enters the lumen (864) of the alignment element (858) and travels through a lumen of the receiving catheter (850). As mentioned above, the deflection surfaces (806, 884, 888, 856) in the delivery, bypass, and receiving catheters (802, 875, 850) may be configured to ease the transition of the wire (820) from the delivery catheter (802) through the vessel walls, into the bypass catheter (875), back through the vessel walls, and into the receiving catheter (850), and guide the wire from the delivery catheter lumen (814) to the bypass catheter lumen (880) and ultimately to the receiving catheter lumen (864). Once a wire path (guidewire bypass) around the occlusion (868) has been established, the delivery, bypass, and receiving catheters (802, 875, 850) may be removed from the vessels to allow for passage of tools or devices along the wire (820).

II. Methods

1. Two Catheter Method

The methods described here may be utilized to advance a wire from a first endoluminal space through one or more luminal walls to a second endoluminal space or cavity. The methods may be used to assist in fistula formation between two endoluminal spaces, for example, between a vein and an artery, between two veins, and the like. Generally, the methods described here comprise accessing a first blood vessel with a first catheter, and advancing the first catheter to a target location within the first blood vessel. The methods generally further comprise accessing a second blood vessel or a body cavity with a second catheter, and advancing the second catheter to a target location within the second blood vessel or the body cavity. In some variations, the first catheter is advanced into an artery, and the second catheter is advanced into a vein. In other variations, the first catheter is advanced into a first vein and the second catheter is advanced into a second vein. In still other variations, the first catheter is advanced into a first artery and the second catheter is advanced into a second artery. In some variations, the first and second catheters may be advanced such that they are in a parallel orientation. In other variations, the first and second catheters may be advanced such that they are in an anti-parallel orientation. The first and/or second catheters may be advanced in any suitable manner, such as using a Seldinger technique or other similar techniques. Advancement may or may not occur under indirection visualization (e.g., via fluoroscopy, X-ray, or ultrasound). The first and second catheters may be advanced in the same manner, or may be advanced in different manners. In variations in which one or both of the catheters are configured for advancement over a guidewire, as described above, the catheters may be advanced along a guidewire. In some variations of the methods described here, one or more external magnets may help advance or position one or both catheters at a target location. In these variations, the external magnets may interact with any suitable portion of the catheter (e.g., one or more magnetic alignment elements) to create an attractive force between the catheter and the external magnet. The attractive force may be used to pull, push, or otherwise manipulate the catheter during advancement.

Once the first and second catheters have been advanced into the respective blood vessels or cavity, the catheters may be adjusted to affect the positioning of the catheters within the blood vessels or cavity and/or the positioning of the blood vessels relative to each other. In variations in which a first catheter has been advanced into a first blood vessel and a second catheter has been advanced into a second blood vessel, the first and second catheters may be aligned or otherwise adjusted to bring at least a portion of the first and second catheters toward each other, which may act to bring the blood vessels in closer approximation. In some variations, each of the first or second catheters may comprise one or more alignment elements, for example, magnetic alignment elements, such as those described in more detail above. The use of magnetic alignment elements may result in an attractive force between the first and second catheters, which may pull the catheters toward each other. In some instances, this attractive force may be sufficient to compress tissue (e.g., blood vessel walls) between the first and second catheters. For example, in variations where the first and second catheters comprise flat surfaces, as described above, the attractive force may flatten and/or compress the tissue between the surfaces.

In some variations, the catheters may be aligned axially and/or rotationally. For example, the catheters may be oriented such that a port on the first catheter may be aligned with a port on the second catheter to create a guidewire path from the first catheter to the second catheter, or vice versa. The catheters may be aligned in any suitable manner. In variations where the first and/or second catheters comprise one or more markers, such as those described above, the markers may be viewed (e.g., via fluoroscopy, x-ray, or the like) to ensure that the catheters have the proper axial and/or radial orientation relative to each other. Additionally, in variations where the first and/or second catheters comprise one or more magnetic alignment elements, the magnetic alignment elements may be used to axially and/or rotationally orient the first catheter relative to the second catheter. Once the catheters have been positioned and aligned, a wire may be used to pierce or otherwise form a hole in the blood vessel wall(s) located between the two catheters and to form a path from the first blood vessel to the second blood vessel or cavity. As mentioned above, after removal of the catheters, the path between the blood vessels may in some variations be used in the creation of a fistula or in another suitable procedure.

It should be appreciated that any of the delivery, receiving, or alignment catheters described above may be used in the methods described here to form a path that may be used in the creation of a fistula. For example, in some variations, the first catheter may be any variation of the delivery catheters described in detail above and the second catheter may be an alignment catheter. In other variations, the first or second catheter may be any variation of the delivery catheters described above, and the other of the first or second catheter may be any variation of the receiving catheters described above.

In some variations, it may be desirable to directionally form the path from the first endoluminal space to the second endoluminal space such that the wire punctures the first luminal wall first and the second luminal wall second (i.e., after puncturing the first luminal wall). For example, in variations in which a wire is advanced and a path is formed between an artery and a vein, it may be desirable to begin in the vein. In these variations, the vein may be punctured prior to puncturing the artery. If one or more catheters malfunctions such that a path between the vein and the artery is not established, beginning in the vein may prevent a puncture in the artery without a corresponding puncture in the vein. When an artery is punctured, the arterial pressure may push blood into the extravascular space around the blood vessels, and in some instances, a surgical procedure may be required to fix the artery. Conversely, puncturing a vein may result in some extravascular bleeding, but the venous pressure may be low enough that significant bleeding does not occur, which may allow the blood vessel to heal itself. While described above as being used to directionally form a path from a vein to an artery, in some instances, it may also be desirable to directionally form a path from an artery to a vein, from a first vein to a second vein, from a first artery to a second artery, from a blood vessel to a cavity, or from a cavity to a blood vessel.

Once a path has been formed between a first vessel and a second vessel, or between a first vessel and a cavity, the catheters described here may be removed from the first and second vessels or from the first vessel and the cavity, and tools may be advanced along the wire to the target locations (e.g., utilizing the wire as a guidewire). Any suitable tools or devices may be advanced, for example, those that may be used to form a fistula between the first and second vessels, or between the first vessel and a cavity, including but not limited to: stents, balloons (including cutting balloons), punching, coring or cutting devices, ablation devices, a combination of thereof, or the like.

In some embodiments, an additional procedure may be performed once the wire has been placed between a first vessel and a second vessel, including but not limited to: the placement of a stent or covered stent through the first and second vessels, which may alter the flow of blood or other bodily fluids; the advancement of a balloon or cutting balloon to the wire location for the purpose of creating a fistula; the advancement of a cutting or ablation device such as a coring tool, radio-frequency cutting electrode, or excimer laser such that tissue may be removed to form a fistula at the location of the wire; and/or the delivery of any percutaneous medical device over the wire and through the vessel walls, such that a device may be advanced from one access location to a different target vessel or system, for example, advancing a device from the venous system into the arterial system.

Turning to FIGS. 9A-9E, shown there is a method for forming a path between two vessels that may be used to guide tools or devices to and/or through the blood vessels. FIG. 9A depicts a first blood vessel (902) and a second blood vessel (908) located adjacent to or near each other in a body. The first blood vessel (902) may comprise a first vessel wall (904) and a first lumen (906), and the second blood vessel (908) may comprise a second vessel wall (910) and a second lumen (912). A first catheter (914) may be advanced through the lumen (906) of the first vessel (902) to a target location within the first vessel (e.g., where puncture and path creation is desired), as can be seen in FIG. 9B. As shown there, the first catheter (914) may be a delivery catheter as described above in detail. A second catheter (916) may be advanced through the lumen (912) of the second vessel (908) to a target location within the second vessel, which may be near or adjacent to the target location in the first vessel (902), as shown in FIG. 9C. As shown there, the second catheter (916) may be a receiving catheter as described above. In some variations, the second catheter may be an alignment catheter, also as described above. In some embodiments of the methods described here, the second catheter (e.g., the receiving or alignment catheter) may be advanced to a target location first, and the first catheter (e.g., the delivery catheter) may be advanced to a target location after advancement of the second catheter. Additionally, while FIG. 9C depicts advancement of the first catheter (914) within the first vessel (902) from a first direction and advancement of the second catheter (916) within the second vessel (908) from a second, opposite direction, such that the two catheters are antiparallel (e.g., the first catheter (914) may comprise an alignment element proximal to the port, and the second catheter (916) may comprise an alignment element distal to the port), this need not be the case. In some variations, the first and second catheters (914, 916) may be advanced within the first and second vessels (902, 908) from the same direction such that the two catheters are parallel (e.g., the catheters may comprise alignment elements proximal to respective ports on the catheters). Additionally, the first and second catheters (914, 916) may be aligned along the lengths of the catheters (as shown), as opposed to at the distal ends of the catheters. Additionally, in some variations, the catheters may have alignment elements on both the proximal and distal sides of the port.

Once the first and second catheters (914, 916) are advanced through the first and second vessels (902, 908) respectively, the first and second catheters (914, 916) may be aligned using the one or more alignment elements (918, 920). For example, in variations in which the alignment elements (918, 920) comprise magnetic alignment elements, the magnetic alignment element (918) on the first catheter (914) may be attracted to the magnetic alignment element (920) on the second catheter (916), which may pull, push, or otherwise move the vessel walls (904, 910) closer to each other. Additionally, the attraction between the magnetic alignment elements (918, 920) may align the ports on the catheters to create a guidewire path from the lumen of the first catheter (914), through the port in the first catheter (914), through the port of the second catheter (916), and into the lumen of the second catheter (916). After the first and second catheters are aligned, a wire (922) may be advanced along the guidewire path to puncture the vessel walls and create a path from the first vessel (902) to the second vessel (908), as shown in FIG. 9D. For example, the wire (922) may be advanced through the lumen and port of the first catheter (914) to the vessel wall (904) of the first vessel (902). It may then pierce the vessel wall (904) at or near the target location within the first vessel, pierce the vessel wall (910) of the second vessel (908) at or near the target location within the second vessel (908), and pass through the port in the second catheter (914) into the lumen of the second catheter (914).

Once the wire (922) has established a path between the first and second catheters (914, 916) and the first and second vessels (902, 908), the first and second catheters (914, 916) may be removed and the wire (922) may remain within the first and second vessels (902, 908) to assist in the advancement of tools or devices, as depicted in FIG. 9E.

In another embodiment, a first catheter in a first vessel may comprise a lumen that may be utilized for advancing a piercing needle and a guidewire within a lumen of the needle. Once the needle has advanced out of the catheter and pierced through the vasculature, a guidewire may be advanced out of the needle. The guidewire may advance into a second vessel adjacent to and/or along an external surface of a second catheter in the second vessel.

Figure 11B:
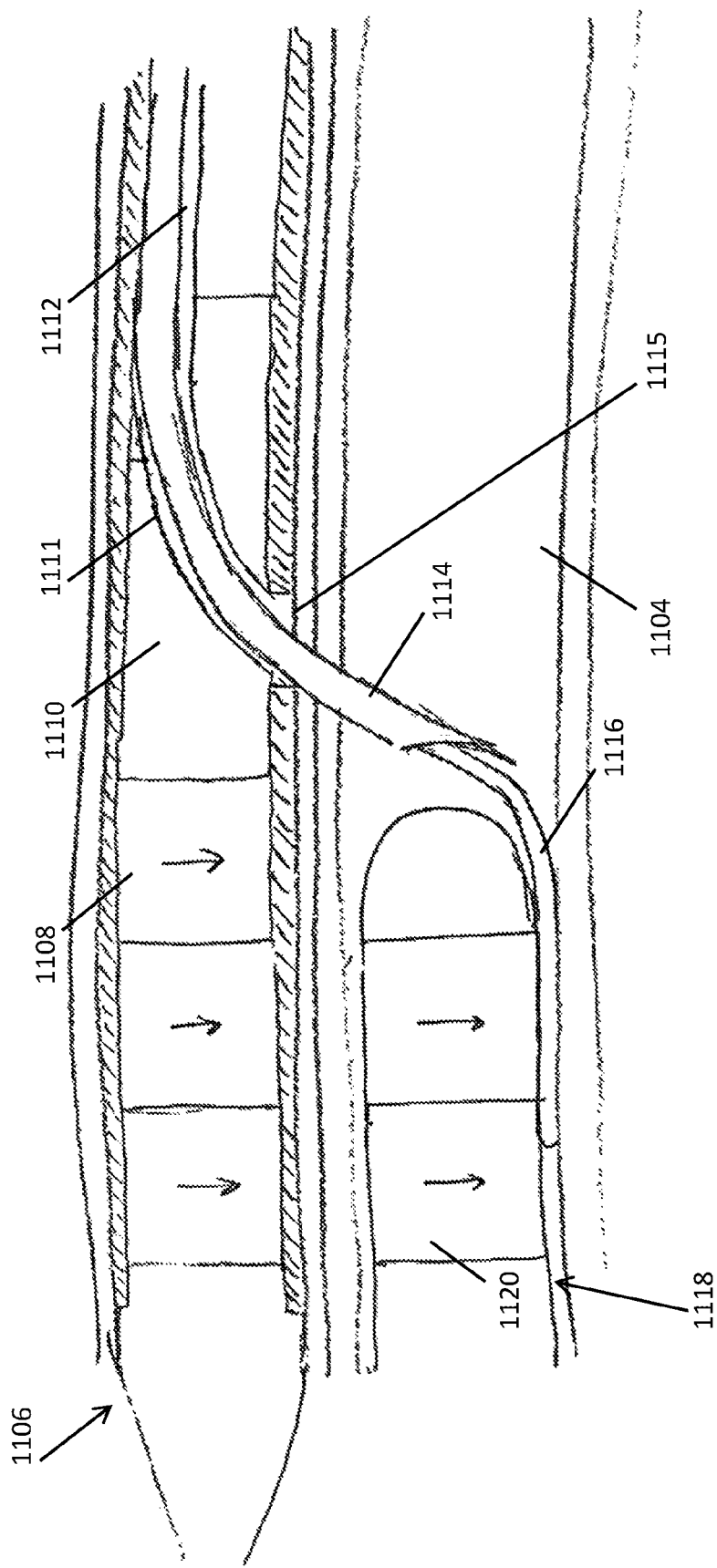

FIGS. 11A-11B illustrate a variation of a system and method for advancing a guidewire, and optionally, a needle, between two vessels. FIG. 11A depicts a first catheter (1106) (e.g., a delivery catheter) disposed within a first vessel (1102) such as an artery, and a second catheter (1118) (e.g., an alignment catheter) disposed within a second adjacent vessel (1104), such as a vein. FIG. 11B depicts a detail view of the first and second catheters (1106, 1118) in use with a flexible needle (1114) and guidewire (1116). In this variation, the first catheter (1106) may be advanced from a first direction and may comprise an alignment element (1108) (e.g., one or more magnets), a deflector (1110) comprising a deflection surface (1111), and a catheter body (1107) comprising a lumen (1112) therethrough and a side port (1115). In some variations, the deflector (1110) and/or the deflection surface (1111) may be formed from the catheter body (1107) (e.g., as the wall of an angled or curved lumen). The lumen (1112) may be provided in a proximal portion of the first catheter (1106) and may fluidly couple a proximal end of the catheter body (1107) and/or a handle or other control coupled thereto (not depicted), to the side port (1115).

In some variations, a flexible needle (1114) may be slideably disposed within the lumen (1112) and may be advanced and/or retracted through the lumen (1112). The flexible needle (1114) may comprise a lumen therethrough and a guidewire (1116) may be slideably disposed within the lumen such that it may be advanced and retracted through the lumen. The deflector (1110) may be disposed within the lumen (1112) of the first catheter (1106) distal to the side port (1115), and may comprise a deflection surface (1111) that may aid in guiding, or otherwise altering the path of, the flexible needle (1114) and the guidewire (1116). In some variations, the deflection surface (1111) may be curved (e.g., concave) to guide one or more of the needle (1114) and the guidewire (1116) through the side port (1115) and out of the first catheter (1106). While described above as comprising both a needle (1114) and a guidewire (1116), the system need not. For example, in some variations, the system may comprise a guidewire (1116) slideably disposed within the lumen (1112) without the use of a needle (1114).

In some variations, the distal end of the needle (1114) may be configured to pierce the vessel walls, while in other variations, including those with and without a needle (1114), the distal end of the guidewire (1116) may be configured to pierce the vessel walls (e.g., the guidewire may comprise a sharpened or beveled distal tip). In some variations, the needle (1114) and/or the guidewire (1116) may be made of a shape-memory material (e.g., nitinol or the like) and may be pre-curved, which may assist in directing the distal tip of the needle (1114) and/or the guidewire (1116) out of the side port (1115) and toward the vessel wall(s). In these variations, a deflector with an angled or curved surface may not be needed.

A second catheter (1118) may be advanced through the second vessel (1104) in a second direction opposite the first direction. The second catheter (1118) may be advanced before or after, the first catheter (1106) is advanced, or concurrently therewith. The first and second catheters (1104, 1106) may each comprise an atraumatic tip, which may assist in preventing damage to tissue as the first and second catheters are advanced through the body. The second catheter (1118) may also comprise an alignment element (1120) (e.g., one or more magnets). In some variations, the first catheter (1106) and the second catheter (1118) may be advanced into the respective vessels and aligned by, for example, the attractive forces of the magnetic alignment elements (1108, 1120). Once both the first and second catheters (1106, 1118) have been advanced through the first and second vessels (1102, 1104) respectively, the first and second catheters (1106, 1118) may be positioned such that the alignment elements (1108) of the first catheter (1106) and the alignment elements (1120) of the second catheter (1118) coapt to compress together with tissue interposed between. The alignment elements (1108, 1120) may assist in appropriately positioning the first catheter (1106) (e.g., the side port (1115)) relative to the vessel wall(s) for advancement of the needle (1114) and/or the guidewire (1116) therethrough. As described above, at least a portion of the catheter bodies may comprise a square cross-sectional shape (e.g., a distal portion), which may also assist in appropriately positioning the first catheter (1106).

The needle (1114) may be advanced through the lumen (1112) of the first catheter (1106) from a proximal portion of the catheter body toward the alignment elements (1108), and the deflector (1110) and the side port (1115) proximal thereto. The deflection surface (1111) of the deflector (1110) may guide the needle (1114) carrying the guidewire (1116) toward the side port (1115) and the vessel walls, such that when the needle (1114) is advanced into the deflection surface (1111) its path is altered from a direction parallel to the longitudinal axis of the first catheter (1106) to a direction transverse to the longitudinal axis of the first catheter (1106).

The needle (1114) may then exit the lumen (1112) of the first catheter (1106) via the side port (1115). In some variations, the distal end of the needle (1114) may puncture the walls of the first and second vessels (1102, 1104) and enter the lumen of the second vessel (1104). In other variations, the guidewire (1116) may be advanced out of the lumen of the needle (1114) to pierce the vessel walls.

Once the distal end of the needle (1114) and/or the guidewire (1116) has entered the lumen of the second vessel (1104), the guidewire (1116) may be advanced, or further advanced, out of the needle (1114) and through the second vessel (1104) (e.g., along the second vessel wall) adjacent and external to the second catheter (1118). As mentioned above, the second catheter (1118) may coapt to the first catheter (1106), which may provide space within the second vessel for advancement of the guidewire (1116) between the second vessel wall and the second catheter (1118), as depicted in FIGS. 11A and 11B. The guidewire (1116) may be advanced to a desired position and the needle (1114) may be retracted back into the first catheter (1106).

2. Three Catheter Method

The methods described here may be utilized to advance a wire from a first endoluminal space (e.g., a vein, an artery, an intestine, and the like) through one or more luminal walls to a second endoluminal space or cavity (e.g., a vein, an artery, an intestine, a cavity surrounding a vessel, and the like), back through the one or more luminal walls into the first endoluminal space. The methods may be used to avoid an occlusion or other barrier within a vessel. For example, the methods may be used to create a wire path from a first occluded vessel at a location upstream of the occlusion, through one or more vessel walls into a second clear vessel or cavity, and back through the one or more vessel walls into the occluded vessel at a location downstream of the occlusion. This wire path may be used to advance tools or devices around an occlusion or barrier.

Generally, the methods described here comprise accessing a first blood vessel from a first direction with a first catheter and advancing the first catheter to a first target location within the first blood vessel, accessing a second blood vessel or a body cavity with a second catheter and advancing the second catheter to a target location within the cavity or the second blood vessel, and accessing the first blood vessel from a second, opposite direction with a third catheter and advancing the third catheter to a second target location within the first blood vessel. In some embodiments, the first vessel may comprise an occlusion or barrier. In these embodiments, the first target location within the first blood vessel may be a location upstream of or proximal to the occlusion or barrier, and the second target location within the first blood vessel may be a location downstream of or distal to the occlusion or barrier.

In some variations, the first and third catheters may be advanced into an artery, and the second catheter may be advanced into a vein. In other variations, the first and third catheters may be advanced into a first vein and the second catheter may be advanced into a second vein. In still other variations, the first and third catheters may be advanced into a first artery and a second catheter may be advanced into a second artery. In still other variations, the first and third catheters may be advanced into a vein, and the second catheter may be advanced into an artery. The first, second, and third catheters may be advanced using the same techniques as described above with respect to the first and second catheters in the two catheter method (e.g., over a guidewire, utilizing external magnets, utilizing visualization techniques). The first, second, and third catheters may be advanced in the same manner, or may be advanced in different manners.

In some variations, the first catheter may be a delivery catheter, as described above. In variations in which a delivery catheter configured for advancement along a guidewire may be used, the first catheter may be advanced to a target location along the guidewire. After the advancement of the second and third catheters, the guidewire may be retracted proximally through the first catheter such that the wire passes through or underneath the deflector to a location proximal to the deflection surface. In some of these embodiments, the same guidewire may then be used to create the bypass path around the occlusion. In some variations, a different wire may be used to create the bypass path around the occlusion. For example, in some instances, a second guidewire, for example, one with a larger diameter, may be used to create the bypass path around the occlusion after the first catheter is advanced to a target location using a first guidewire. In these variations, the first guidewire may be retracted proximally through the first catheter after the catheter is advanced to a target location and before advancement of the second guidewire. The first guidewire may optionally be removed from the first catheter through an opening in the handle or a proximal portion of the first catheter.

Once the first, second, and third catheters have been advanced into the respective blood vessels or cavity, the catheters may be aligned or otherwise adjusted to affect the positioning of the catheters within the blood vessels or cavity and/or the positioning of the blood vessels relative to each other. In variations in which the first and third catheters have been advanced into a first blood vessel and a second catheter has been advanced into a second blood vessel, the first, second, and third catheters may be adjusted to bring at least a portion of the first and third catheters toward the second catheter, which may act to bring the blood vessels in closer approximation. In some variations, each of the first, second, and third catheters may comprise one or more alignment elements, for example, magnetic alignment elements, such as those described in more detail above. The use of magnetic alignment elements may result in an attractive force between the first and second catheters and the second and third catheters, which may pull the catheters toward each other. In some instances, this attractive force may be sufficient to compress tissue (e.g., blood vessel wall(s)) between the first and second and second and third catheters. For example, in variations where the first, second, and third catheters comprise flat surfaces, as described above, the attractive force may flatten and/or compress vessel tissue between the surfaces.

In some variations, the first, second, and third catheters may be aligned axially and/or rotationally. For example, the catheters may be oriented such that a port on the first catheter may be aligned with a first port on the second catheter, and a second port on the second catheter may be aligned with a port on the third catheter. This alignment may create a guidewire path from the first catheter, through the second catheter, to the third catheter. The catheters may be aligned in any suitable manner. The first, second, and third catheters may comprise one or more markers, as described above, which may be viewed (e.g., via fluoroscopy, x-ray, or the like) to ensure that the catheters have the proper axial and/or radial orientation relative to each other. Once the catheters have been positioned and adjusted, a wire may be used to puncture the blood vessel wall(s) located between the catheters and form a path from the first blood vessel to the cavity or the second blood vessel and back into the first blood vessel.

It should be appreciated that any of the delivery or receiving catheters described above may be used in the methods described here to form a path that may be used to bypass an occlusion or barrier within a vessel. For example, in some variations, the first catheter may be any variation of the delivery catheters described in detail above and the third catheter may be any variation of the receiving catheters described above. In other variations, the third catheter may be any variation of the delivery catheters described above, and the first catheter may be any variation of the receiving catheters described above. In some embodiments, the second catheter may be any variation of the bypass catheters described above.

Once a path has been formed around an occlusion or barrier in a vessel, the catheters described here may be removed from the first and second vessels or from the first vessel and the cavity, and tools may be advanced along the wire around the occlusion or barrier (e.g., utilizing the wire as a guidewire). Any suitable tools or devices may be advanced, for example, those that may be used to form a fistula between the first and second vessels, or between the first vessel and a cavity (e.g., stents, balloons (including cutting balloons), punching, coring or cutting devices, ablation devices, or the like), stents or stent-grafts, and a combination thereof, and the like. Additionally, the methods described here may be used in percutaneous in-situ fem-pop bypass procedures, or for recapture and externalization of a wire.

Figure 10D:
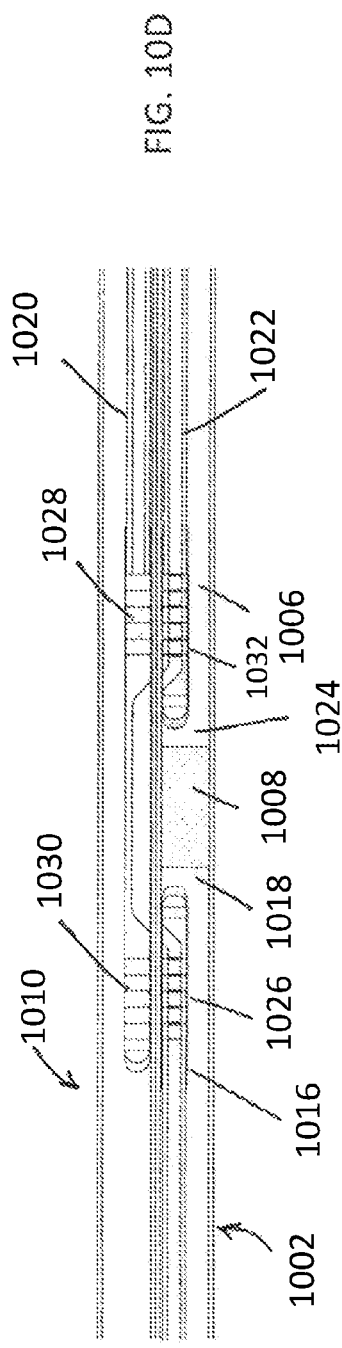
Figure 10E:
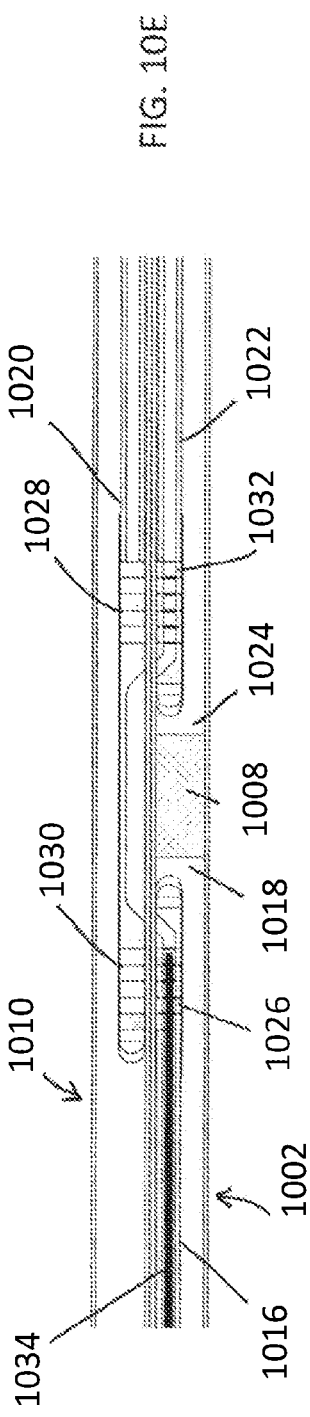

FIGS. 10A-10J depict a method for bypassing an occlusion in a vessel as described here. Specifically, FIG. 10A depicts a first blood vessel (1002) located adjacent to or near a second blood vessel (1010). The first blood vessel (1002) may comprise a first vessel wall (1004), a lumen (1006), and an occlusion (1008), and the second blood vessel (1010) may comprise a second vessel wall (1012), and a lumen (1014). As shown in FIG. 10B, a first catheter (1016) may be advanced through the lumen (1006) of the first blood vessel (1002) from a first direction toward a first side (1018) of the occlusion (1008) to a first target location within the first vessel (e.g., a location upstream of the occlusion at the desired exit location of the wire). As shown there, the first catheter (1016) may be a delivery catheter as described above in detail. Turning to FIG. 10C, a second catheter (1020) may be advanced through the lumen (1014) of the second blood vessel (1010) to a target location within the second vessel, which may be near or adjacent to the first (and second, as described below) target location(s) in the first blood vessel (1002). In some variations, the target location in the second vessel may be at a location corresponding to the occlusion (1008) in the first vessel (1002). The second catheter (1020) may be a bypass catheter as described above. Moving to FIG. 10D, a third catheter (1022) may be advanced through the lumen (1006) of the first blood vessel (1002) from a second, opposite direction to a second, opposite side (1024) of the occlusion to a second target location within the first vessel (e.g., a location downstream of the occlusion at the desired reentrance location of the wire). As shown there, the third catheter (1022) may be a receiving catheter, a described above. In some variations, the first catheter (1016) may be a receiving catheter as described above, and the third catheter (1022) may be a delivery catheter as described above.

Although the first, second, and third catheters are described as being advanced in numerical order, this need not be the case. The first, second, and third catheters may be advanced in any order. For example, in some variations, the third catheter may be advanced first, followed by the second catheter and the first catheter, while in other variations, third catheter may be advanced first followed by the first catheter and the second catheter. In yet other variations, the first catheter may be advanced first, followed by the third catheter, and the second catheter. In yet other variations, the second catheter may be advanced first, followed by the first and third catheters in any order. In some instances, the catheters may be advanced simultaneously.

Once the first and third catheters (1016, 1022) are advanced through the first blood vessel (1002) and the second catheter (1020) is advanced through the second blood vessel (1010), the first, second, and third catheters (1016, 1020, 1022) may be aligned using the one or more alignment elements (1026, 1028, 1030, 1032), as shown in FIG. 10D. For example, in variations in which the alignment elements (1026, 1028, 1030, 1032) comprise magnetic alignment elements, the magnetic alignment element (1026) on the first catheter (1016) may be attracted to the second magnetic alignment element (1030) on the second catheter (1020), and the magnetic alignment element (1032) on the third catheter (1022) may be attracted to the first magnetic alignment element (1028) on the second catheter (1020). In some variations, the catheters may be configured such that the magnetic alignment element (1026) on the first catheter (1016) may be attracted to the first magnetic alignment element (1028) on the second catheter (1020), and the magnetic alignment element (1032) on the third catheter (1022) may be attracted to the second magnetic alignment element (1030) on the second catheter (1020). The attraction between the corresponding magnetic alignment elements may pull, push, or otherwise move the vessel walls closer to each other. Additionally, the attraction between corresponding magnetic alignment elements may align the ports on the catheters to create a guidewire path from the lumen of the first catheter (1016), through the port in the first catheter (1016), through the first port of the second catheter (1020), into the lumen of the second catheter (1020) to the second port of the second catheter (1020), through the second port of the second catheter, through the port on the third catheter (1022), and into the lumen of the third catheter (1022). Additionally, the first, second, and third catheters (1016, 1020, 1022) may be configured such that the catheters are aligned along the lengths of the catheters (as shown), as opposed to at their distal ends.

Figure 10F:
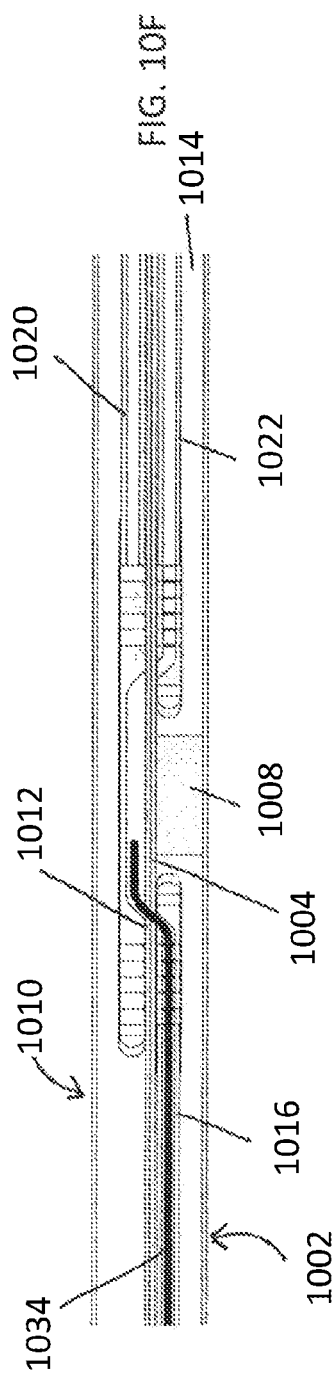

After the first, second, and third catheters are aligned, a wire (1034) may be advanced along the guidewire path to pierce the vessel walls and create a wire path from the first vessel (1002) to the second vessel (1010), back through the vessel walls to the first vessel (1002) to bypass the occlusion (1008) in the lumen (1006) of the first vessel (1002), as shown in FIGS. 10E-10H. For example, the wire (1034) may be advanced through the lumen of the first catheter (1016) (FIG. 10E), through the port in the first catheter (1016) and the first blood vessel wall (1004) at a location proximal to the occlusion (1008). The wire (1034) may pierce the second blood vessel wall (1012), and may be advanced therethrough to and through the first port of the second catheter (1020), and through the lumen of the second catheter (1020) at the location of the occlusion (1008) in the first blood vessel lumen (1014) (FIG. 10F). The wire (1034) may then be advanced through the second port of the second catheter (1020) to pierce the second vessel wall (1012) and the first vessel wall 1004) at a location distal to the occlusion (1008) (FIG. 10G). The wire (1034) may then enter the third catheter (1022) through the port and continue into the lumen of the third catheter (1022) (FIG. 10H).

Once the wire (1034) has bypassed the occlusion (1008) and established a guidewire bypass around the occlusion (1008) between the first, second, and third catheters (1016, 1020, 1022) and the first and second vessels (1002, 1010), the second catheter (1020) may be removed without disrupting or otherwise severing the path around the occlusion (FIG. 10I). For example, as discussed in more detail above, the second catheter may comprise a slit or other opening that may allow passage of the wire (1034) therethrough such that the second catheter (1020) may be removed from the second blood vessel (1010) without advancement or retraction of the wire (1034). The first and third catheters (1016, 1022) may also be removed from the first blood vessel lumen (1006) such that only the wire (1034) remains (FIG. 10J). Finally, tools or devices, as described above, may be advanced around the occlusion (1008) using the wire (1034) (e.g., as a guide wire).

Although the foregoing variations have, for the purposes of clarity and understanding, been described in some detail by way of illustration and example, it will be apparent that certain changes and modifications may be practiced, and are intended to fall within the scope of the appended claims. Additionally, it should be understood that the components and characteristics of the devices and methods described herein may be used in any appropriate combination. The description of certain elements or characteristics with respect to a specific figure are not intended to be limiting or nor should they be interpreted to suggest that the element cannot be used in combination with any of the other described elements.

We claim:

1. A system for advancing a crossing wire through a vessel wall comprising:
    a first catheter comprising a catheter body having a first lumen therethrough and a first side aperture, a first deflection surface, a first alignment element and a second alignment element positioned on either side of the first side aperture within the first lumen, wherein the first deflection surface is positioned between the first alignment element and the second alignment element;
    a second catheter comprising a catheter body having a second lumen therethrough and a second side aperture, a second deflection surface, and a third alignment element and a fourth alignment element positioned on either side of the second aperture within the second lumen; and
    a crossing wire,
    wherein the first, second, third, and fourth alignment elements are configured to align the first and second side apertures to create a crossing wire pathway through the first and second catheters, wherein the second catheter further comprises a guide funnel positioned directly adjacent the second deflection surface and between the second deflection surface and the second lumen and configured to direct a distal tip of the crossing wire into the second lumen.

2. The system of claim 1, wherein the first catheter is a delivery catheter and the second catheter is a receiving catheter.

3. The system of claim 1, wherein the first, second, third, and fourth alignment elements each comprise a magnet or a magnetic array.

4. The system of claim 1, wherein a second deflection surface is positioned between the third and fourth alignment elements.

5. The system of claim 1, wherein the first alignment element is configured to mate with the third alignment element and the second alignment element is configured to mate with the fourth alignment element.

6. The system of claim 1, wherein the first and second catheters are configured to be aligned lengthwise.

7. The system of claim 1, wherein the first alignment element comprises a lumen configured to pass the crossing wire therethrough.

8. The system of claim 7, wherein the fourth alignment element comprises a lumen configured to pass the crossing wire therethrough.

9. The system of claim 1, wherein the first catheter comprises a first deflector positioned within the first lumen and comprising the first deflection surface and the second catheter comprises a second deflector positioned within the second lumen and comprising the second deflection surface.

10. The system of claim 1, wherein the first and second catheters are arranged so that slopes of the first and second deflection surfaces have the same sign.

11. The system of claim 1, wherein one or both of the first and second deflection surfaces are curved.

12. The system of claim 1, wherein the guide funnel configured to direct the distal tip of the crossing wire into the second lumen has a first diameter at a first end and a second diameter at a second end, wherein the second diameter is smaller than the first diameter.

13. The system of claim 1, wherein the first and second catheters each comprise an atraumatic tip.

14. The system of claim 1, wherein at least a portion of each of the catheter bodies of the first and second catheters comprise a square cross-sectional shape in an axial direction.

15. The system of claim 1, wherein the first catheter defines a guidewire lumen extending alongside the first lumen and intersecting the first deflection surface to extend longitudinally past to a distal end of the first catheter.

* * * * *